(12) United States Patent
Middleton et al.

(10) Patent No.: US 6,746,451 B2
(45) Date of Patent: Jun. 8, 2004

(54) TISSUE CAVITATION DEVICE AND METHOD

(76) Inventors: Lance M. Middleton, 490 Booth Hill Rd., Trumbull, Fairfield County, CT (US) 06611; Laura H. Middleton, 490 Booth Hill Rd., Trumbull, Fairfield County, CT (US) 06611

( * ) Notice: Subject to any disclaimer, the term of this patent is extended or adjusted under 35 U.S.C. 154(b) by 0 days.

(21) Appl. No.: 09/872,042

(22) Filed: Jun. 1, 2001

(65) Prior Publication Data

US 2002/0183758 A1 Dec. 5, 2002

(51) Int. Cl.$^7$ ............................................... A61B 17/32
(52) U.S. Cl. ........................... 606/79; 606/80; 606/180
(58) Field of Search ................................. 606/180, 181, 606/182, 183, 79, 80, 159; 408/203, 204, 205, 178, 173

(56) References Cited

U.S. PATENT DOCUMENTS

| | | | |
|---|---|---|---|
| 3,030,951 A | | 4/1962 | Mandarino |
| 3,320,957 A | * | 5/1967 | Sokolik ................. 606/170 |
| 4,751,922 A | * | 6/1988 | DiPietropolo ............ 606/80 |
| 4,969,888 A | | 11/1990 | Scholten et al. |
| 5,030,201 A | | 7/1991 | Palestrant |
| 5,062,845 A | | 11/1991 | Kuslich et al. |
| 5,108,404 A | | 4/1992 | Scholten et al. |
| 5,376,100 A | | 12/1994 | Lefebvre |
| 5,403,317 A | * | 4/1995 | Bonutti ................. 606/180 |
| 5,431,671 A | | 7/1995 | Nallakrishnan |
| 5,445,639 A | | 8/1995 | Kuslich et al. |
| 5,556,429 A | | 9/1996 | Felt |
| 5,658,310 A | | 8/1997 | Berger et al. |
| 5,693,011 A | | 12/1997 | Onik |
| 5,695,513 A | | 12/1997 | Johnson et al. |
| 5,720,749 A | * | 2/1998 | Rupp .................... 606/180 |
| 5,827,289 A | | 10/1998 | Reiley et al. |
| 5,843,103 A | * | 12/1998 | Wulfman ................ 606/159 |
| 5,888,220 A | | 3/1999 | Felt et al. |
| 5,925,056 A | | 7/1999 | Thomas et al. |
| 5,928,239 A | | 7/1999 | Mirza |
| 5,935,131 A | | 8/1999 | Bonutti |

(List continued on next page.)

FOREIGN PATENT DOCUMENTS

| EP | 0442137 B1 | 8/1991 |
|---|---|---|
| EP | 442137 A1 | 8/1991 |

OTHER PUBLICATIONS

Biomedical Enterprises, Inc., "Bone Grafting," Dec. 9, 1998, All Pages, Published by Biomedical Enterprises, Inc. in the United States of America on the Internet at www/bme-tx.com/grafting.html.
U.S. patent application Ser. No. 10/284,672, Middleton, filed Oct. 31, 2002.
U.S. patent application Ser. No. 60/336,557, Middleton, filed Nov. 1, 2001.

Primary Examiner—Pedro Philogene
(74) Attorney, Agent, or Firm—Gardere Wynne Sewell LLP

(57) ABSTRACT

A percutaneous surgical device and method for creating a cavity within tissue during a minimally invasive procedure. A cavitation device includes a shaft interconnected to a flexible cutting element. A flexible cutting element has a first shape suitable for minimally invasive passage into tissue. The flexible cutting element has a means to move toward a second shape suitable for forming a cavity in tissue. When used in bone, the resulting cavity is usually filled with bone cement or suitable bone replacement material that is injectable and hardens in situ. The disclosed cavitation device and methods can be used for the following applications: (1) treatment or prevention of bone fracture, (2) joint fusion, (3) implant fixation, (4) tissue harvesting (especially bone), (5) removal of diseased tissue (hard or soft tissue), and (6) general tissue removal (hard or soft tissue).

64 Claims, 15 Drawing Sheets

U.S. PATENT DOCUMENTS

| | | |
|---|---|---|
| 5,972,015 A | 10/1999 | Scribner et al. |
| 6,066,154 A | 5/2000 | Reiley et al. |
| 6,071,284 A | 6/2000 | Fox |
| 6,139,509 A | 10/2000 | Yuan et al. |
| 6,140,452 A | 10/2000 | Felt et al. |
| 6,171,312 B1 | 1/2001 | Beaty |
| 6,224,604 B1 | 5/2001 | Suddaby |
| 6,235,043 B1 | 5/2001 | Reiley et al. |
| 6,238,391 B1 | 5/2001 | Olsen et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,296,639 B1 * | 10/2001 | Truckai et al. .............. 606/41 |
| 6,383,188 B2 * | 5/2002 | Kuslich et al. ............. 408/158 |
| 2002/0022856 A1 * | 2/2002 | Johnson et al. ............ 606/185 |

* cited by examiner

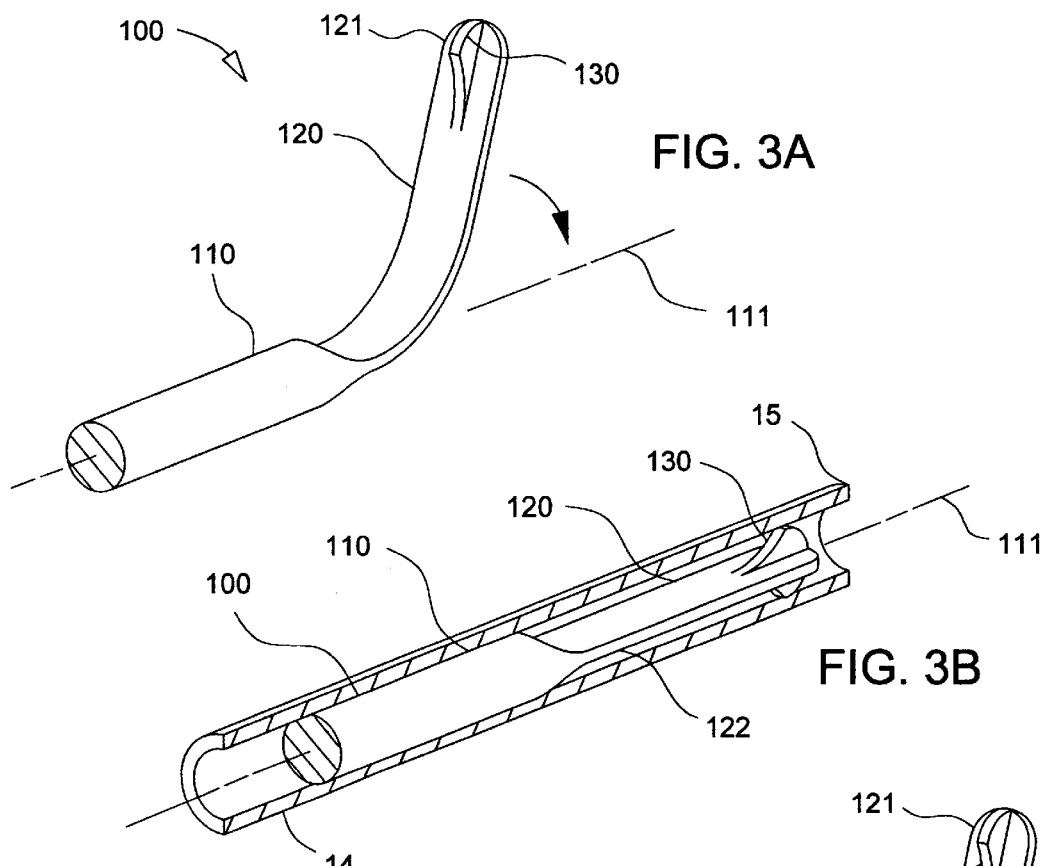
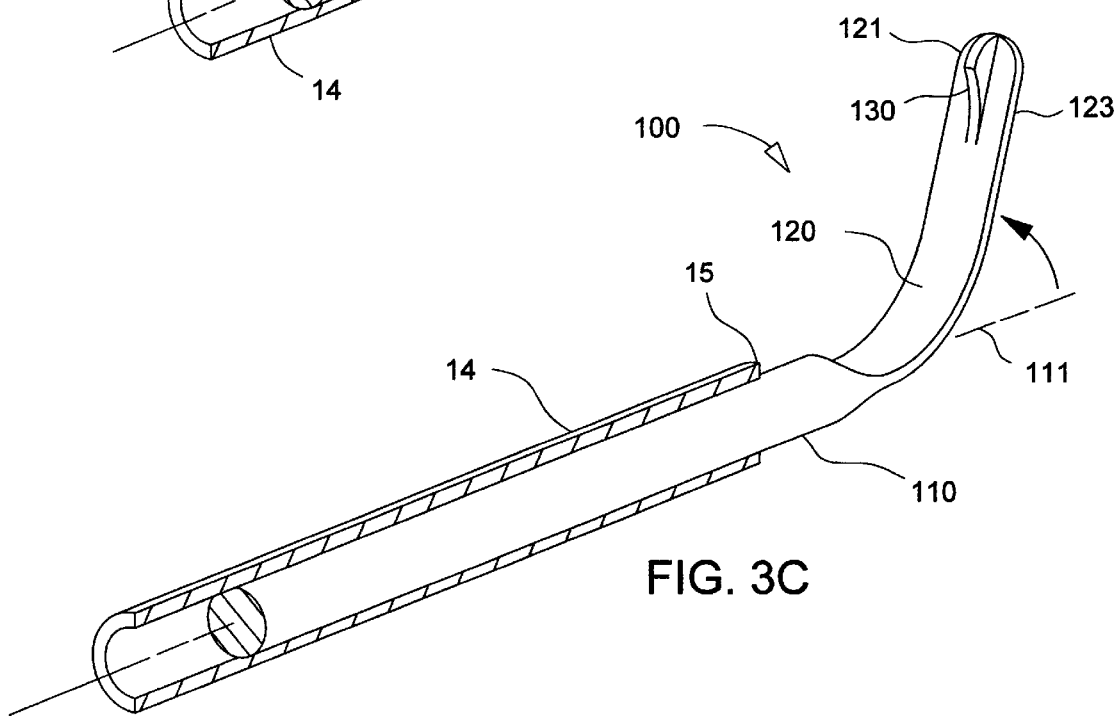

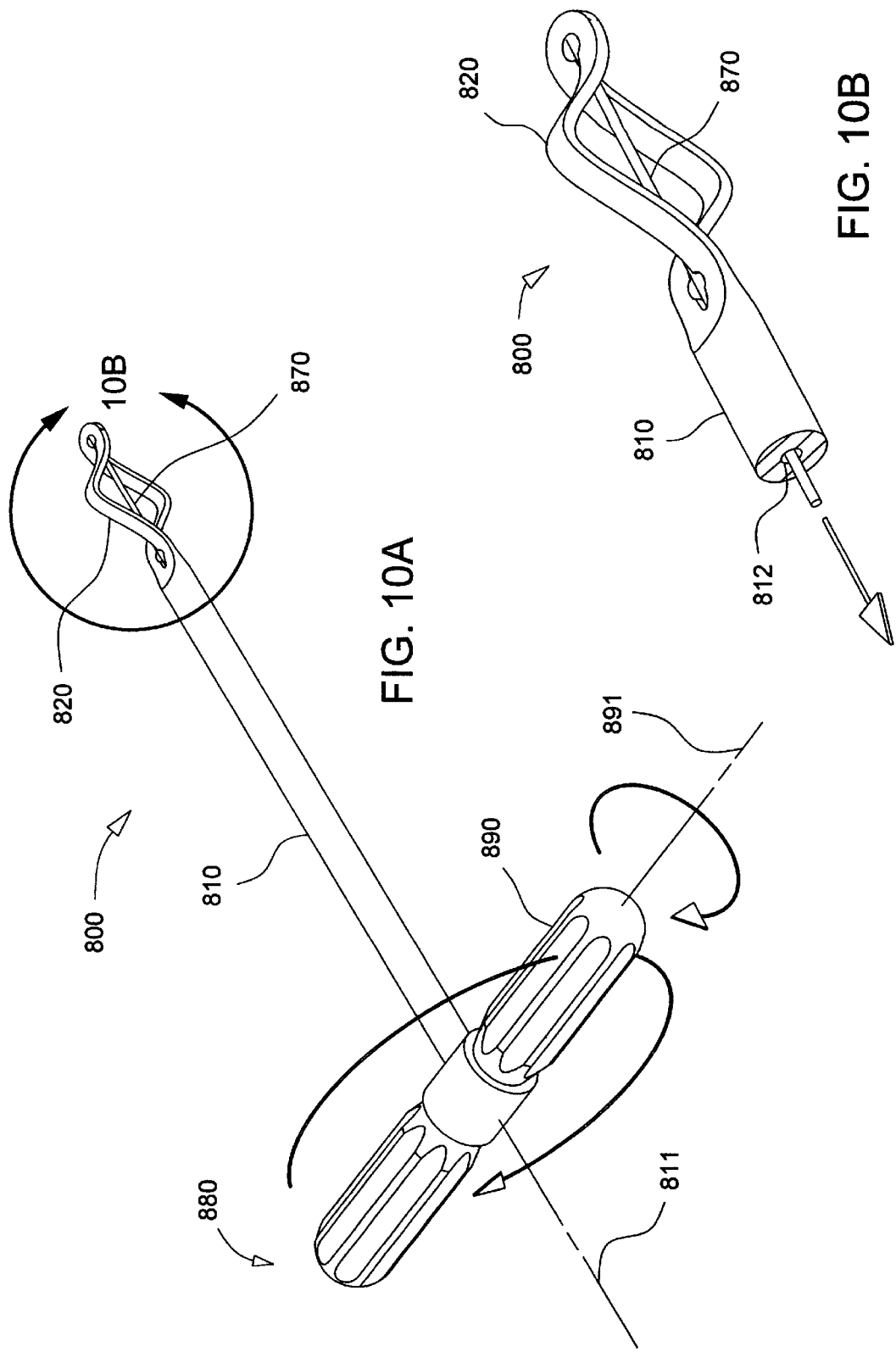

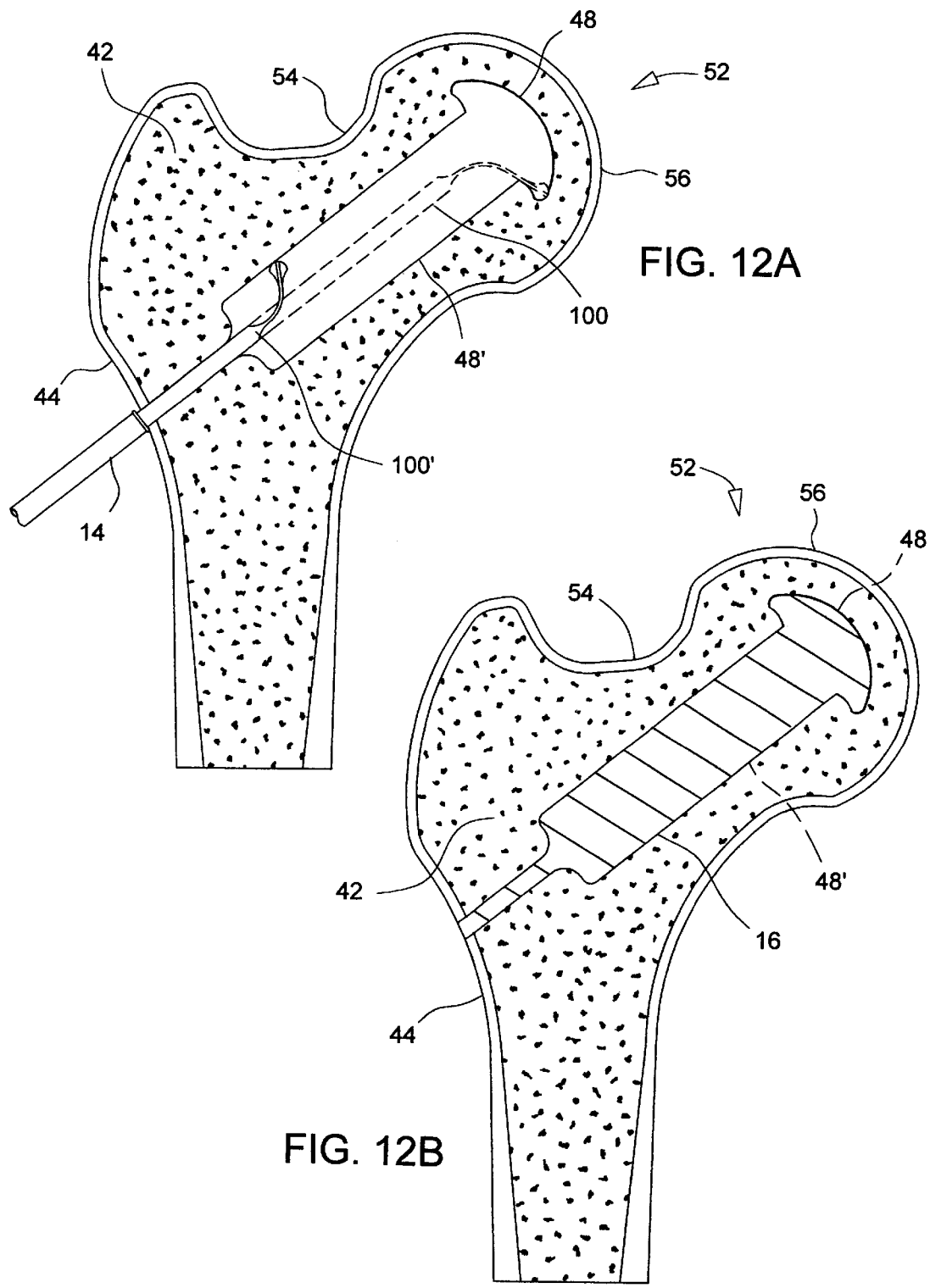

TISSUE CAVITATION DEVICE AND METHOD

FIELD OF THE INVENTION

The present invention relates generally to surgical devices and methods and, more particularly, to minimally invasive surgical devices and methods for creating a cavity within hard or soft tissue.

BACKGROUND OF THE INVENTION

Surgeons are using minimally invasive surgical techniques on an increasing basis for the treatment of a wide variety of medical conditions. Such techniques typically involve the insertion of a surgical device through a natural body orifice or through a relatively small incision using a tube or cannula. In contrast, conventional surgical techniques, typically involve a significantly larger incision and are therefore sometimes referred to as open surgery. Thus, as compared with conventional techniques, minimally invasive surgical techniques offer the advantages of minimizing trauma to healthy tissue, minimizing blood loss, reducing the risk of complications such as infection, and reducing recovery time. Further, certain minimally invasive surgical techniques can be performed under local anesthesia or even, in some cases, without anesthesia, and therefore enable surgeons to treat patients who would not tolerate the general anesthesia required by conventional techniques.

Surgical procedures often require the formation of a cavity within either soft or hard tissue, including bone. Tissue cavities are formed for a wide variety of reasons, such as for the removal of diseased tissue, for harvesting tissue in connection with a biopsy or autogenous transplant, and for implant fixation. To achieve the benefits associated with minimally invasive techniques, tissue cavities should be formed by creating only a relatively small access opening in the target tissue. An instrument or device can then be inserted through the opening and used to form a hollow cavity that is significantly larger than the access opening. Depending on the specific application, the shape of the desired cavity can be spherical, hemispherical, cylindrical, or any number of different combinations or variations of such shapes.

One important surgical application requiring the formation of a cavity within tissue is the surgical treatment and prevention of skeletal fractures associated with osteoporosis, which is a metabolic disease characterized by a decrease in bone mass and strength. The disease leads to skeletal fractures under light to moderate trauma and, in its advanced state, can lead to fractures under normal physiologic loading conditions. It is estimated that osteoporosis affects approximately 15–20 million people in the United States and that approximately 1.3 million new fractures each year are associated with osteoporosis, with the most common fracture sites being the hip, wrist and vertebrae.

An emerging prophylactic treatment for osteoporosis involves replacing weakened bone with a stronger synthetic bone substitute using minimally invasive surgical procedures. The weakened bone is first surgically removed from the affected site, thereby forming a cavity. The cavity is then filled with an injectable synthetic bone substitute and allowed to harden. The synthetic bone substitute provides structural reinforcement and thus lessens the risk of fracture of the affected bone. Without the availability of minimally invasive surgical procedures, however, the prophylactic fixation of osteoporosis-weakened bone in this manner would not be practical because of the increased morbidity, blood loss and risk of complications associated with conventional procedures. Moreover, minimally invasive techniques tend to preserve more of the remaining structural integrity of the bone because they minimize surgical trama to healthy tissue.

Other less common conditions in which structural reinforcement of bone can be appropriate include bone cancer and avascular necrosis. Surgical treatment for each of these conditions can involve removal of the diseased tissue by creating a tissue cavity and filling the cavity with a stronger synthetic bone substitute to provide structural reinforcement to the affected bone.

Existing devices for forming a cavity within soft or hard tissue are relatively complex assemblies consisting of multiple components. U.S. Pat. No. 5,445,639 to Kuslich et al. discloses an intervertebral reamer for use in fusing contiguous vertebra. The Kuslich et al. device comprises a cylindrical shaft containing a mechanical mechanism that causes cutting blades to extend axially from the shaft to cut a tissue cavity as the shaft is rotated. The shaft of the Kuslich et al. device, however, has a relatively large diameter in order to house the blade extension mechanism, and therefore it is necessary to create a relatively large access opening to insert the device into the body. The complexity of the device leads to increased manufacturing costs and may also raise concerns regarding the potential for malfunction.

U.S. Pat. No. 5,928,239 to Mirza discloses a percutaneous surgical cavitation device and method useful for forming a tissue cavity in minimally invasive surgery. The Mirza device comprises an elongated shaft and a separate cutting tip that is connected to one end of the shaft by a freely-rotating hinge, as shown in FIG. 1 hereto. The cutting tip of the Mirza device rotates outward about the hinge, thereby permitting the device to cut a tissue cavity that is larger than the diameter of the shaft. However, the Mirza device relies on rotation of the shaft at speeds ranging from 40,000 to 80,000 rpm to cause the cutting tip to rotate outward about the hinge. Such high rotational speeds can only be produced by a powered surgical drill and certainly cannot be produced by manual rotation. Thus, the Mirza device does not permit the surgeon to exercise the precise control that can be attained through manual rotation. Moreover, there may be a concern for structural failure or loosening of the relatively small hinge assembly at such a high rotational speed when operated in bone. The high rotational speed of the Mirza device may also generate excessive heat that could damage healthy tissue surrounding the cavity.

U.S. Pat. No. 6,066,154 to Reiley et al. discloses an inflatable, balloon-like device for forming a cavity within tissue. The Reiley et al. device is inserted into the tissue and then inflated to form the cavity by compressing surrounding tissue, rather than by cutting away tissue. The Reiley et al. device, however, is not intended to cut tissue, and at least a small cavity must therefore be cut or otherwise formed in the tissue in order to initially insert the Reiley et al. device.

Thus, a need continues to exist for a tissue cavitation device and method that can form tissue cavities of various shapes that are significantly larger than the access opening in the target tissue. A need also exists for a cavitation device that is of relatively simple construction and inexpensive to manufacture, that can be operated either manually or by a powered surgical drill, and that, in the case of manual operation, provides the surgeon with increased control over the size and shape of the cavity formed.

SUMMARY OF THE INVENTION

The present invention comprises an improved tissue cavitation device and method that utilizes shape-changing behavior to form cavities in either hard or soft tissue. The shape-changing behavior enables the device to be inserted into tissue through a relatively small access opening, yet also enables the device to form a tissue cavity having a diameter larger than the diameter of the access opening. Thus, the invention is particularly useful in minimally invasive surgery, and can be used for at least the following specific applications, among others: (1) treatment or prevention of bone fracture, (2) joint fusion, (3) implant fixation, (4) tissue harvesting (especially bone), (5) removal of diseased tissue (hard or soft tissue), and (6) general tissue removal (hard or soft tissue).

The cavitation device of the present invention comprises a rotatable shaft having a flexible cutting element that is adapted to move between a first shape and a second shape during the process of forming an internal cavity within tissue. The process of forming the cavity primarily involves cutting tissue as the shaft is rotated about its longitudinal axis, but those skilled in the art will appreciate that the device also can form a cavity by impacting tissue or displacing tissue as the shaft is either partially or completely rotated. The internal cavity formed by the device has a significantly larger diameter than the diameter of the initial opening used to insert the device into the tissue. The present invention also comprises flexing means for biasing the flexible cutting element to move from its first shape to its second shape. One such means comprises spring bias arising from elastic deformation of the flexible cutting element. A second such means comprises bias arising from the behavior of a thermal shape-memory alloy. A third such means comprises bias arising from centrifugal force generated as the shaft is rotated. A fourth such means comprises a tension cable that forcefully actuates the shape change of the flexible cutting element. The device of the invention can be operated by conventional surgical drills, and some embodiments also can be manually operated using a conventional T-handle. When a T-handle is used to operate the device, the T-handle also can be adapted to apply tension to the tension cable.

During minimally invasive surgery, the flexible cutting element of the cavitation device can be adapted to assume a first shape for insertion of the device into tissue through a tube placed percutaneously, thereby creating only a relatively small access opening in the tissue. Depending on the application and size, the insertion tube can be a trochar, a cannula, or a needle. As the device is inserted beyond the distal end of the insertion tube, the flexible cutting element is adapted to assume a second shape for forming a cavity in tissue upon rotation of the shaft. When it assumes the second shape, the flexible cutting element extends or projects away from the longitudinal axis of the shaft. Thus, the diameter of the cavity is greater than the diameter of the initial access opening or pilot hole. In addition to cutting, a flexible cutting element is capable of displacing and impacting tissue away from the axis of the shaft.

According to one method of the present invention, the periphery of the target tissue, such as bone, can be accessed with an insertion tube placed percutaneously, and a pilot hole can be formed in the bone with a standard surgical drill and drill bit. Next, the cavitation device of the present invention is inserted to the depth of the pilot hole and rotated. As the flexible cutting element of the device moves from its first shape to its second shape, portions of the cutting element forcefully extend away from the longitudinal axis of the shaft, thereby forming a tissue cavity. Emulsified bone can be removed through known irrigation and suction methods. In the case of bone harvesting, the abated bone is used at another surgical site to promote healing of a bony deficit or to promote joint fusion. The cavity can then be filled with a suitable bone substitute that is injectable and hardens in situ. In the case of removing and replacing osteoporotic bone, the cavity is filled with structural synthetic bone or bone cement. Since the device and methods of the present invention are minimally invasive, they can be used for the prevention of osteoporosis related fractures in individuals at high risk. Skeletal structures where osteoporosis related fractures are common include the radius, femur, and vertebral bodies.

Surgeons can create cavities of various shapes and sizes with the device and methods of the present invention. For example, cavities of various shapes and sizes can be formed by moving the cavitation device along its axis of rotation or transverse to its axis of rotation. The size and shape of the cavity also can be modified by adjusting the insertion angle of the shaft (or the insertion tube, if one is used) with respect to the tissue angle. Tissue cavities of various shapes and sizes also can be interconnected to form more complex shapes.

The objects and advantages of the present invention include simplicity, wherein a flexible cutting element eliminates the need for complex assemblies with numerous moving parts. The shape-changing behavior of the flexible cutting element enables the device to be adapted to a shape suitable for minimally invasive placement in tissue. The inherent outward forces associated with the shape change of the flexible cutting element assist in the cutting and displacement of tissue during the process of forming a cavity.

BRIEF DESCRIPTION OF THE DRAWINGS

FIGS. 3A to 3C are perspective views showing a first embodiment of the cavitation device of the present invention.

FIG. 10A is a perspective view showing a seventh embodiment of the cavitation device of the present invention attached to a T-handle.

FIG. 10B is a detailed view showing the flexible cutting element of the device shown in FIG. 10A.

FIG. 12A is a sectional view of the proximal end of the human femur showing a cavitation device of the present invention creating a cavity to remove osteoporotic bone.

FIG. 12B shows the cavity of FIG. 12A filled with a synthetic bone substitute to strengthen the femur.

DETAILED DESCRIPTION OF THE PREFERRED EMBODIMENTS

Figure 1:
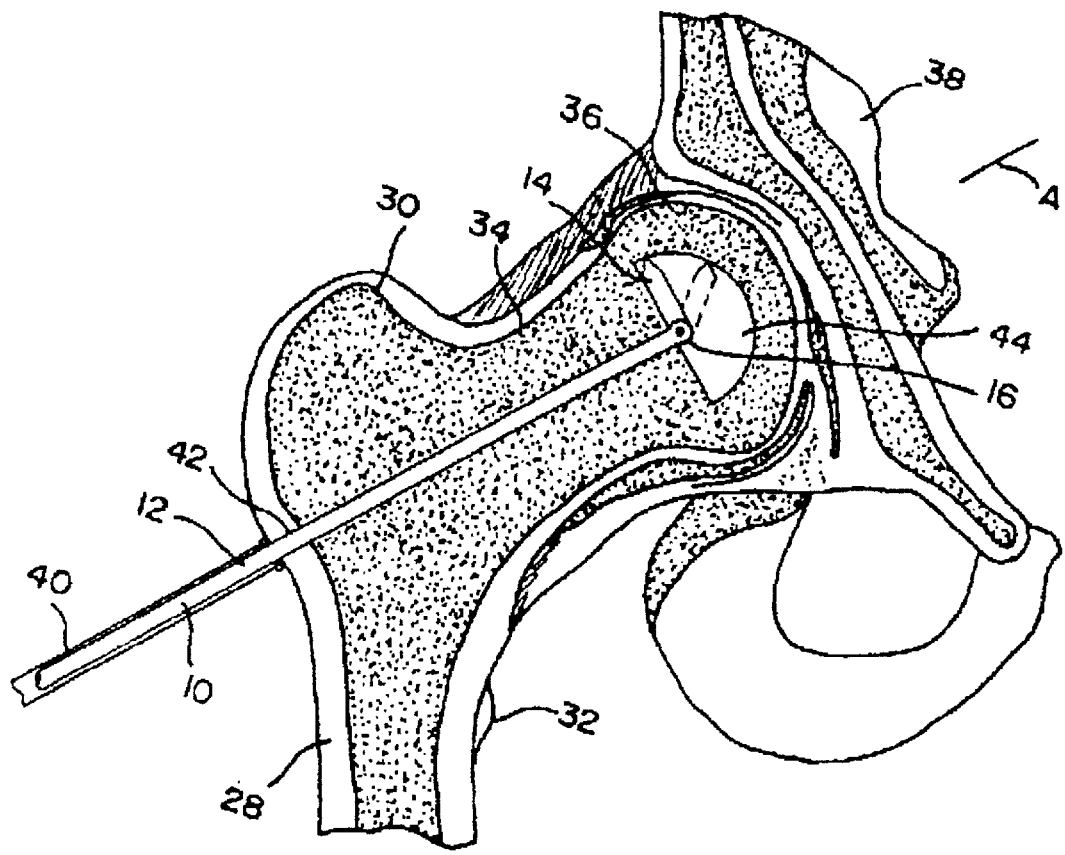
FIG. 1 is a sectional view of the proximal end of the human femur and shows the prior art cavitation device disclosed in U.S. Pat. No. 5,928,239 to Mirza.
Figure 2A:
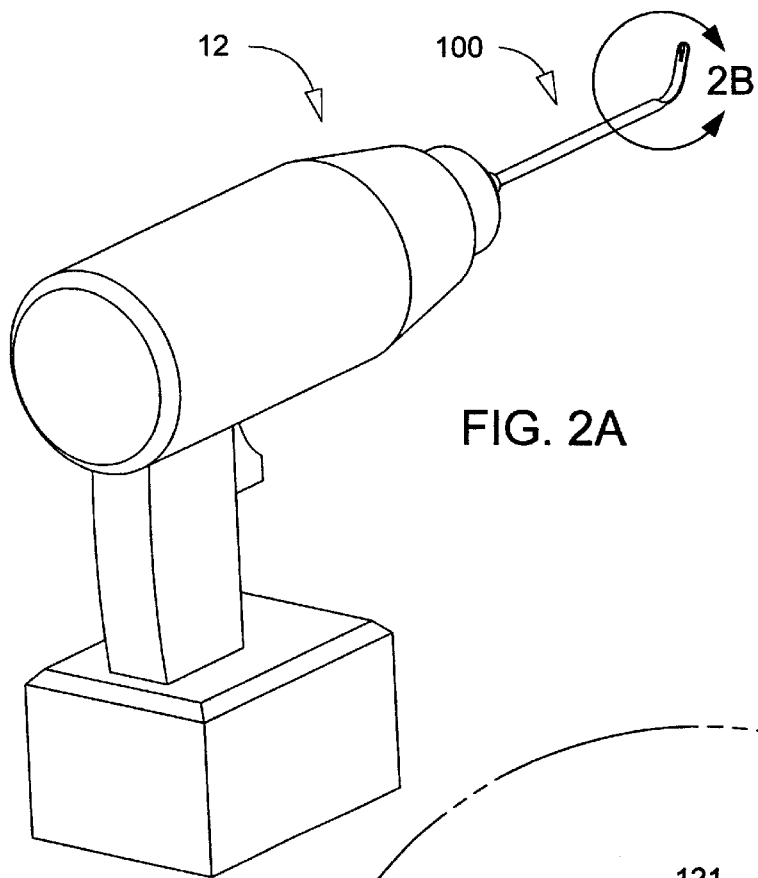
FIG. 2A is a perspective view showing a cavitation device of the present invention attached to a surgical drill.

Throughout the following description and the drawings, like reference numerals are used to identify like parts of the present invention. FIG. 2A shows a cavitation device 100 of the present invention attached to a surgical drill 12. Surgical drill 12 is battery powered and is shown to illustrate one possible means of operation. There are numerous other options for either powered or manual operation of cavitation device 100. For powered operation, the device can be used with a variety of readily available surgical drills that are pneumatic or electric, such as drills manufactured by Mathys International, Ltd. For manual operation, the shaft of the device can be connected to a conventional T-handle, which is a surgical device that is well known to those skilled in the art. A supplier of a multi-purpose T-handle is Beere Precision Medical Instruments.

Figure 2B:
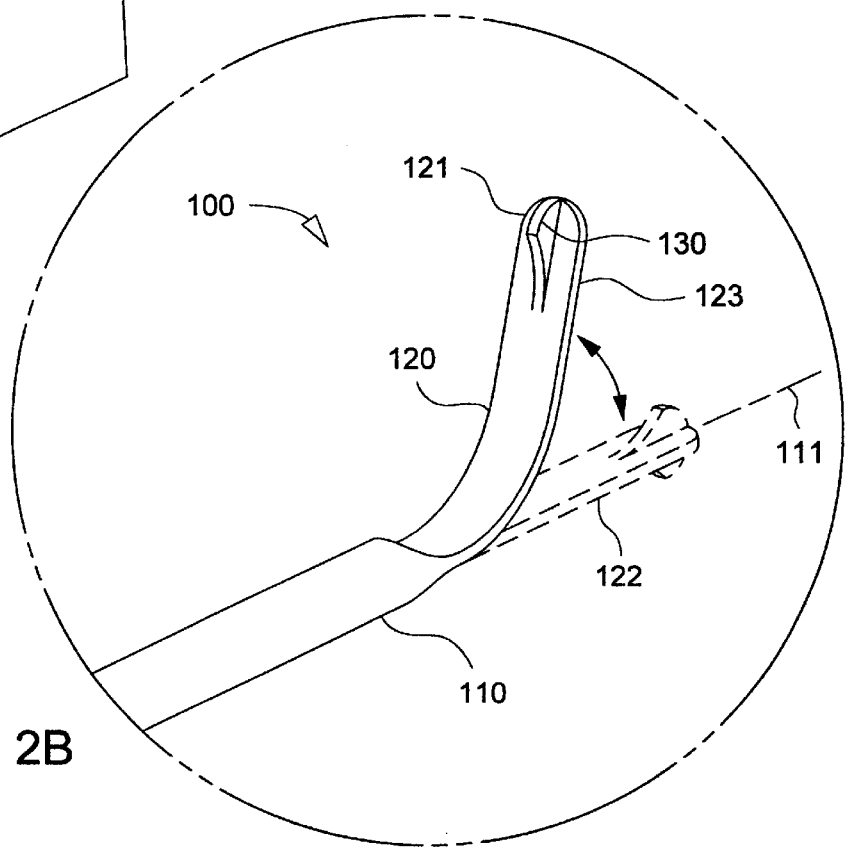
FIG. 2B is a detailed view of the distal end of the device depicted in FIG. 2A and shows a flexible cutting element.

As shown in FIG. 2B, cavitation device 100 comprises a rotatable shaft 110, a flexible cutting element 120, and a cutting tip 130. Rotatable shaft 110 has a longitudinal axis 111 and preferably has a generally circular cross-section, but other cross-sections, such as a generally square cross-section, are within the scope of the invention. The diameter of rotatable shaft 110 is typically within a range of about 3 to 8 millimeters for minimally invasive surgery. However, other diameters outside this range also are within the scope of the invention. Flexible cutting element 120 is disposed at one of the two ends of rotatable shaft 110 and is preferably formed from the same piece of material as rotatable shaft 110 for added strength and durability. Those skilled in the art will appreciate that the integrally formed construction of rotatable shaft 110 and flexible cutting element 120 also reduces manufacturing costs. Flexible cutting element 120 has a free end 121 and a relatively thin, rectangular cross-section. Thus, flexible cutting element 120 is consistent with a machine element known as a leaf spring and also is consistent with a structural element known as a cantilever beam. Because of this configuration, flexible cutting element 120 is adapted to flex between a first shape 122, in which flexible cutting element 120 is substantially colinear with the longitudinal axis 111 of rotatable shaft 110, and a second shape 123, in which flexible cutting element 120 extends or projects away from longitudinal axis 111 in the general shape of a curvilinear arc, as shown in FIG. 2B.

FIGS. 3A to 3C further illustrate the shape-changing behavior of cavitation device 100. As shown in FIG. 3A, when flexible cutting element 120 is in its initial, undeformed state (i.e., spring unloaded), it extends or projects away from longitudinal axis 111 of rotatable shaft 110. However, as shown in FIG. 3B, cavitation device 100 is dimensioned to pass telescopically through the interior of an insertion tube 14. Depending on the particular surgical application, insertion tube 14 can be a trochar, a cannula, or a needle. As cavitation device 100 is placed within insertion tube 14, flexible cutting element 120 experiences elastic deformation (i.e., spring loaded) and assumes first shape 122, in which flexible cutting element 120 is substantially colinear with longitudinal axis 111. Cutting tip 130 helps to keep flexible cutting element 120 aligned within insertion tube 14 as it is passed telescopically through insertion tube 14. Referring now to FIG. 3C, as flexible cutting element 120 extends past the distal end 15 of insertion tube 14, flexing means, which in this embodiment is spring bias arising from elastic deformation, tends to move flexible cutting element 120 from first shape 122 toward second shape 123. Consistent with spring mechanics, flexible cutting element 120 seeks to return to second shape 123 because it is a spring unloaded configuration. By reversing the insertion process, cavitation device 100 can be removed through the insertion tube 14.

Cavitation device 100 can be constructed from a wide spectrum of surgical-grade stainless steels capable of elastic behavior. Consistent with spring mechanics, it is preferred to have the shape change of flexible cutting element 120 operate within the elastic range of the material. Stainless steels are strong, relatively inexpensive, and their manufacturing processes are well understood. Another suitable material is the metal alloy Nitinol (TiNi), a biomaterial capable of superelastic mechanical behavior, meaning that it can recover from significantly greater deformation compared to most other metal alloys. The Nitinol metal alloy contains almost equal parts of titanium and nickel. Nitinol has a "spring-back" potential ten times greater than stainless steels and is capable of nearly full recovery from 8% strain levels. Suppliers of Nitinol include Shape Memory Applications, Inc. and Nitinol Devices & Components. Alternatively, cavitation device 100 can be constructed from a polymer, such as nylon or ultra high molecular weight polyethylene.

A thermal shape-memory alloy can also be used as a flexing means for biasing a flexible cutting element to move from a first shape to a second shape. The most commonly used biomaterial with thermal shape-memory properties is the Nitinol metal alloy. A flexible cutting element made from Nitinol can be deformed below a transformation temperature to a shape suitable for percutaneous placement into tissue. The reversal of deformation is observed when the flexible cutting element is heated through the transformation temperature. The applied heat can be from the surrounding tissue, or associated with frictional heat generated during operation. Nitinol is capable of a wide range of shape-memory transformation temperatures appropriate for the clinical setting, including a transformation temperature at body temperature of 37° C. Heat may also be applied by passing electrical current through the material to cause resistive heating.

Figure 4A:
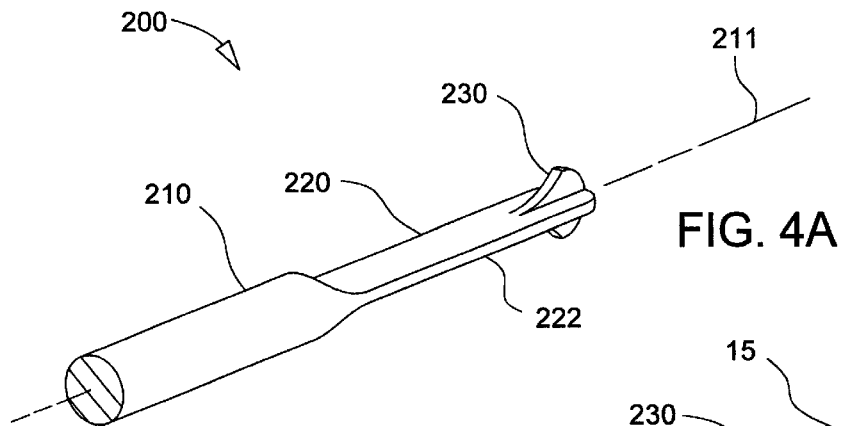
FIGS. 4A to 4C are perspective views showing a second embodiment of the cavitation device of the present invention.
Figure 4B:
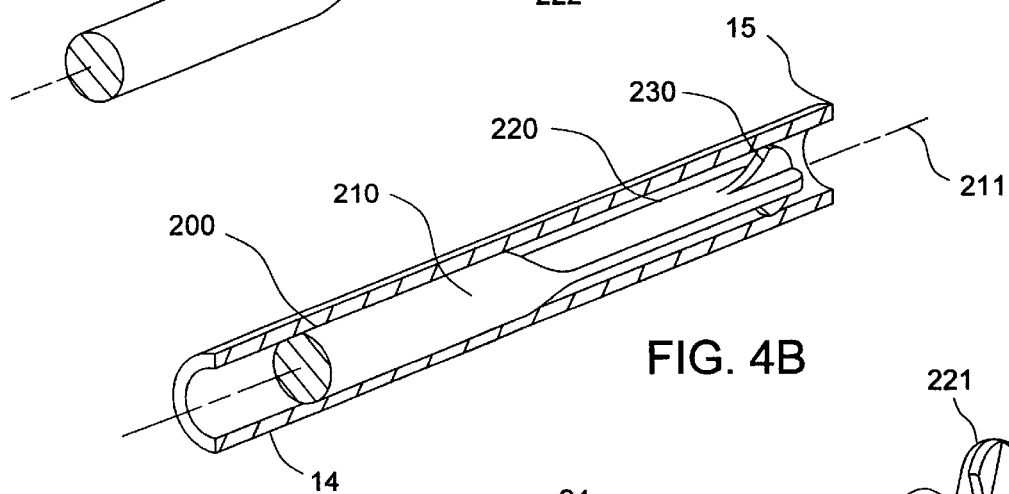
Figure 4C:
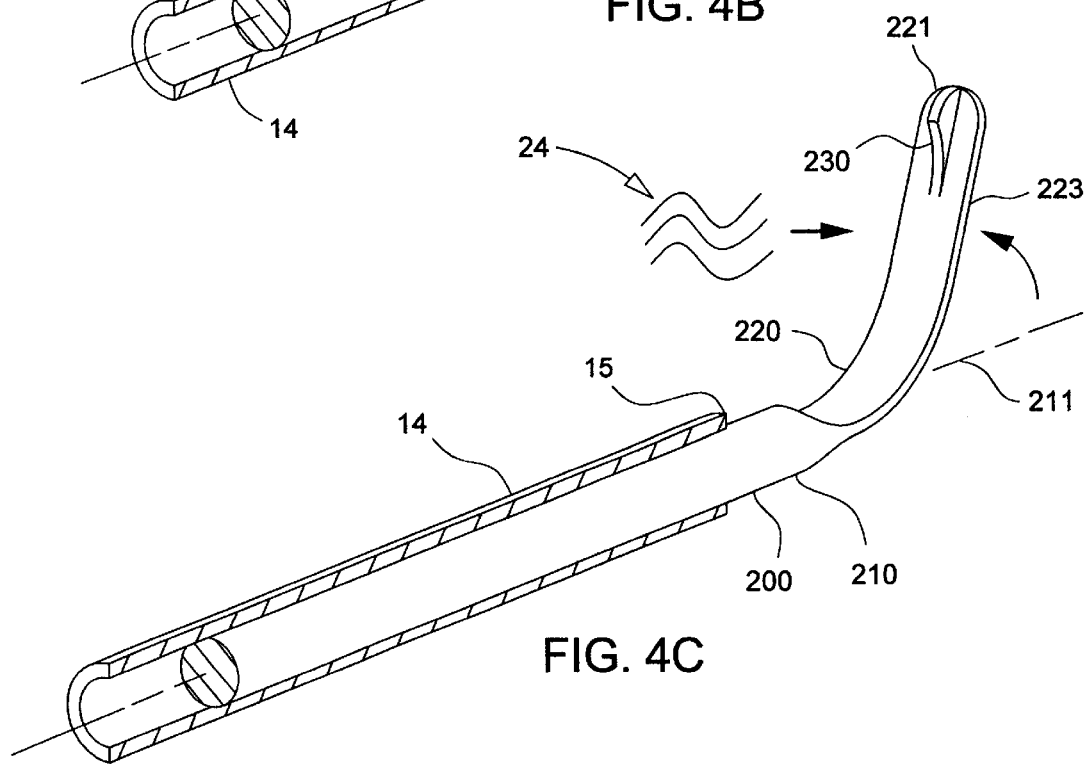

FIGS. 4A to 4C show a second embodiment of the present invention, cavitation device 200, comprising rotatable shaft 210 and a flexible cutting element 220 having a free end 221 and a cutting tip 230. Flexible cutting element 220 is formed from a material, such as Nitinol, which is capable of shape change arising from thermal shape-memory behavior. Rotatable shaft 210 has a longitudinal axis 211. FIG. 4A shows cavitation device 200 at rest, with flexible cutting element 220 deformed below the transformation temperature to a first shape 222 in which flexible cutting element 220 is substantially colinear with longitudinal axis 211. When flexible cutting element 220 is in first shape 222, cavitation device 200 can be easily passed telescopically through the interior of an insertion tube 14, as shown in FIG. 4B. Referring now to FIG. 4C, as flexible cutting element 220 extends past distal end 15 of insertion tube 14, applied heat 24 activates the thermal shape-memory properties of flexible cutting element 220. Applied heat 24 can be body heat from the patient or operational heat, such as heat generated from friction. Flexible cutting element 220 has a bias toward a "remembered" second shape 223, in which flexible cutting element 220 extends or projects away from longitudinal axis 211 of rotatable shaft 210 in the general shape of a curvilinear arc, as shown in FIG. 4C. Elastic properties of flexible cutting element 220 allow removal of cavitation device 200 through the insertion tube 14.

Figure 5A:
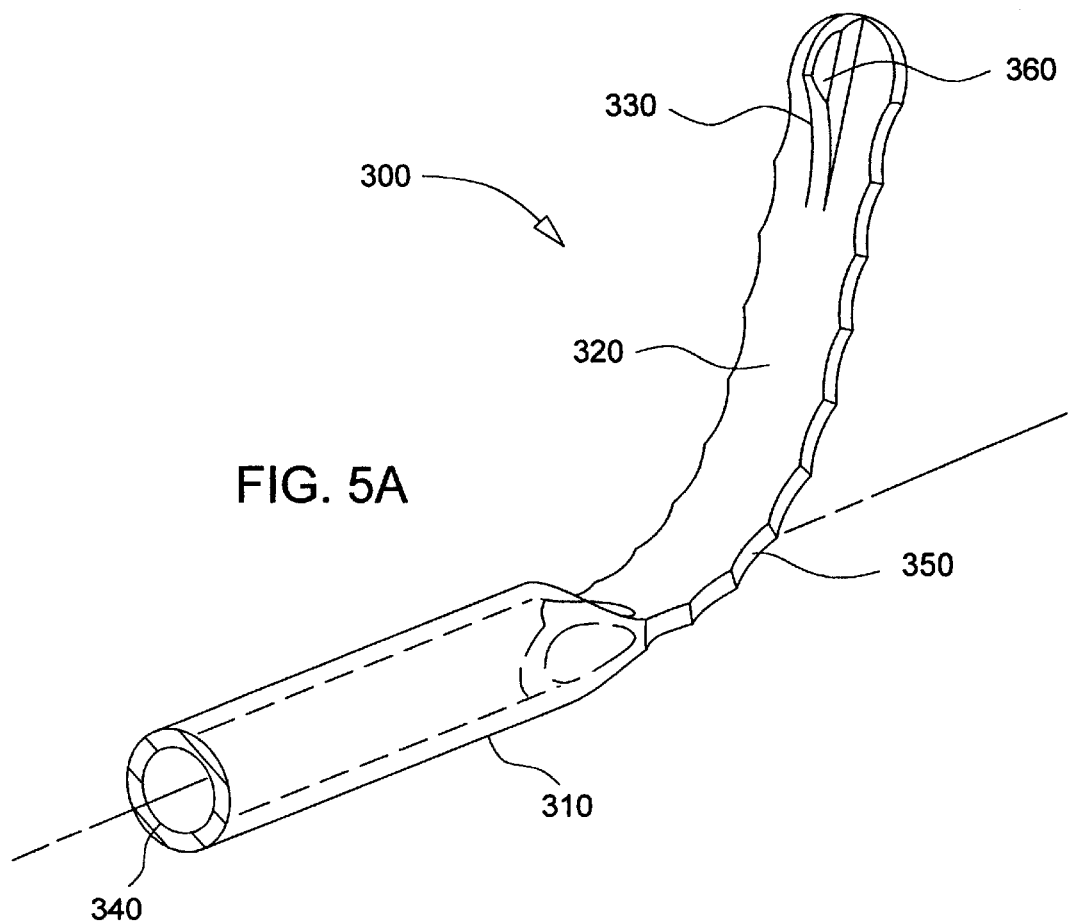
FIGS. 5A and 5B are perspective views showing a cavitation device of the present invention having serrations, cutting flutes and an irrigation passage as additional features.
Figure 5B:
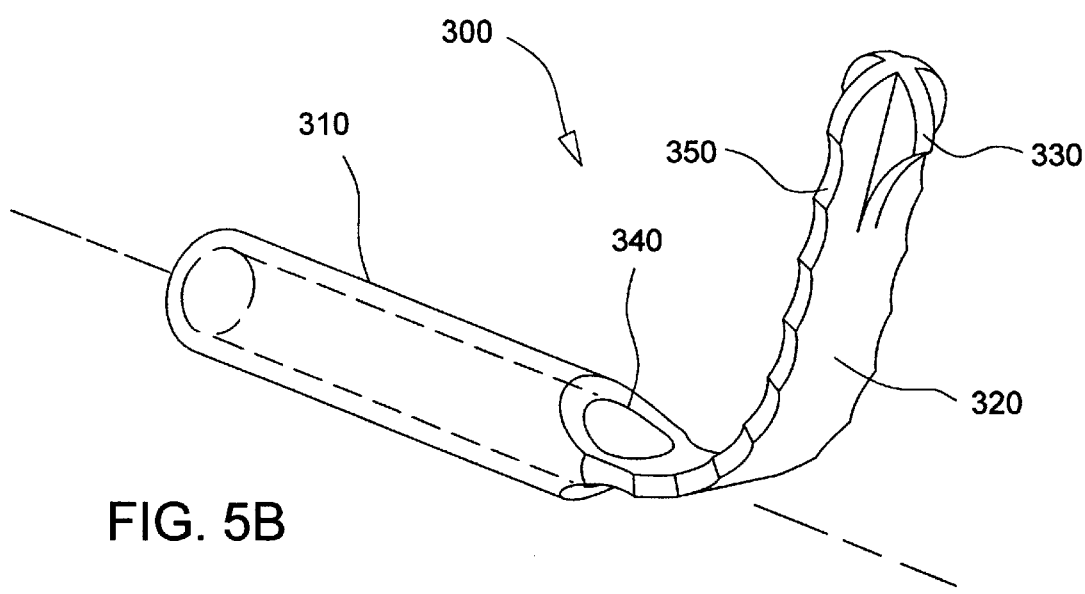

It may be advantageous to add additional features to enhance the performance of a cavitation device of the present invention and to enhance the process of cavity creation or tissue removal. Numerous secondary features to aid in tissue cutting include serrated edges, threads, cutting flutes, abrasive surfaces, and beveled edges. Variations and different combinations are possible without departing from the spirit of the present invention. Referring now to FIGS. 5A and 5B, cavitation device 300 can comprise serrations 350 to aid in tissue cutting. Similarly, cutting tip 330 can comprise a cutting flute 360 to aid in tissue cutting. Cavitation device 300 also can comprise an irrigation passage 340, which serves as a conduit for tissue irrigation and removal through rotatable shaft 310.

Figure 6:
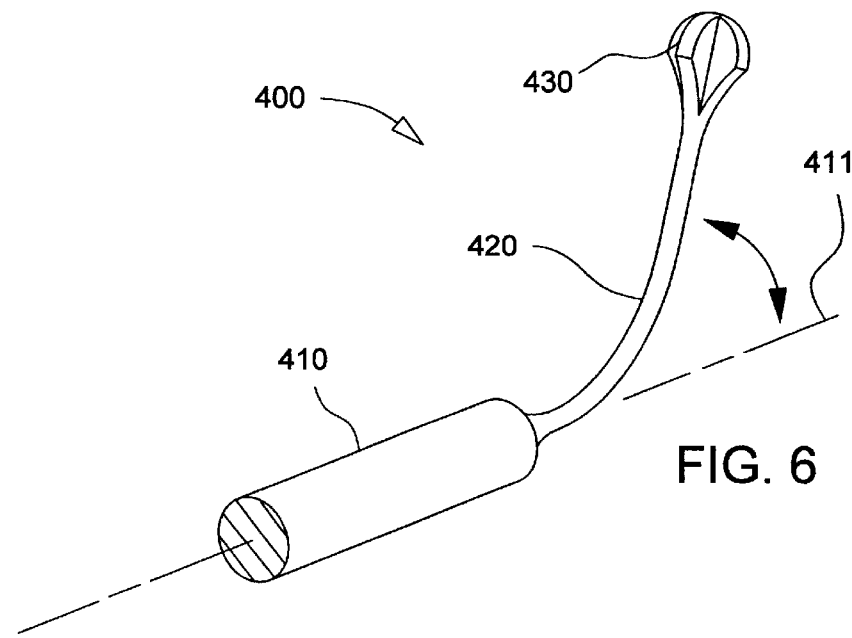
FIG. 6 is a perspective view showing a third embodiment of the cavitation device of the present invention.
Figure 7A:
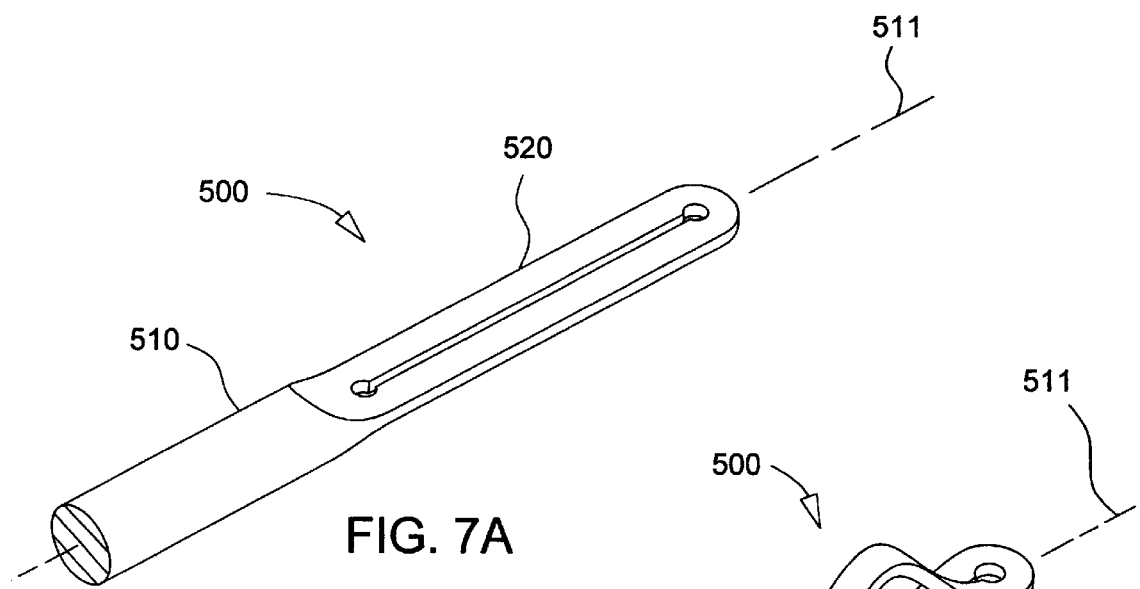
FIGS. 7A and 7B are perspective views showing a fourth embodiment of the cavitation device of the present invention.
Figure 7B:
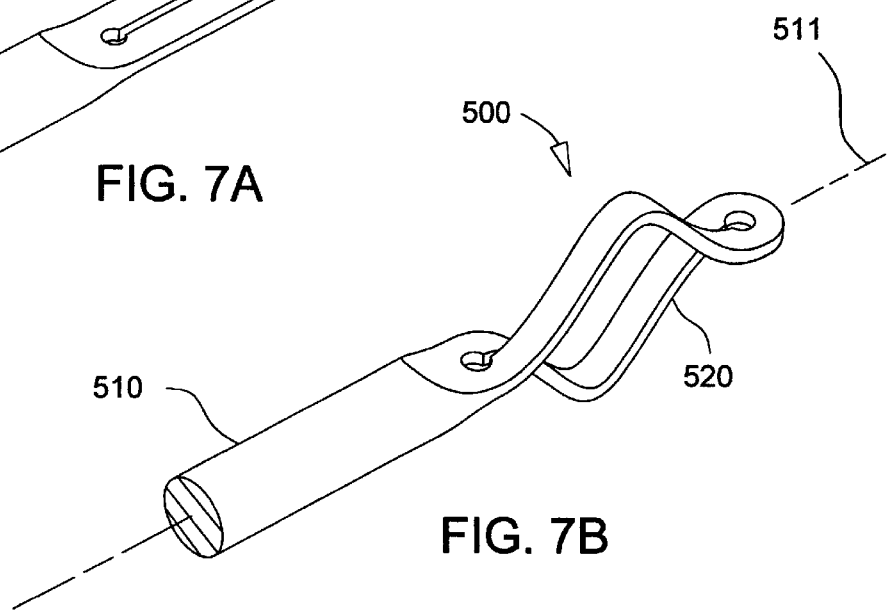

Geometric variations, within the spirit of the present invention, may be developed to enhance or alter the performance of the dynamic shape behavior. Examples of such variations include the cross-sectional shape and the length of a flexible cutting element. For example, the cross-sectional shape of the flexible cutting element can form a quadrilateral so that the edges formed from the acute angles of the quadrilateral are adapted to aid in cutting. A quadrilateral cross-section with a particularly acute angle can form a knife-edge. Persons skilled in the art will understand that a flexible cutting element with a quadrilateral cross-section and a beveled edge would have a substantially quadrilateral cross-section and that a rectangular cross-section is a substantially quadrilateral cross-section. Further, the curvature of a flexible cutting element in the extended position may take a specific shape; therefore the shape of the tissue cavity need not be limited to combinations of cylindrical and hemispherical tissue cavities. Different tissue cavity shapes may be desirable for interfacing with an implant or to create a region of synthetic bone to match complex anatomical structures. In addition, a plurality of flexible cutting elements can be used, rather than a single flexible cutting element. As an example, FIG. 6 shows a third embodiment of the present invention, cavitation device 400, comprising a rotatable shaft 410 having longitudinal axis 411. Cavitation device 400 further comprises flexible cutting element 420 which has a generally a circular cross-section. Further, as shown in FIG. 7A, a fourth embodiment of the invention, cavitation device 500, comprises a rotatable shaft 510 and a plurality of flexible cutting elements 520. FIG. 7A shows cavitation device 500 with flexible cutting elements 520 substantially colinear with longitudinal axis 511 of rotatable shaft 510, consistent with a first shape suitable for minimally invasive placement within tissue. Referring now to FIG. 7B, flexible cutting elements 520 are shown in a second shape, in which portions of flexible cutting elements 520 extend or project away from longitudinal axis 511. Note that flexible cutting elements 520 form a closed loop that can take a specific shape if required.

Figure 8A:
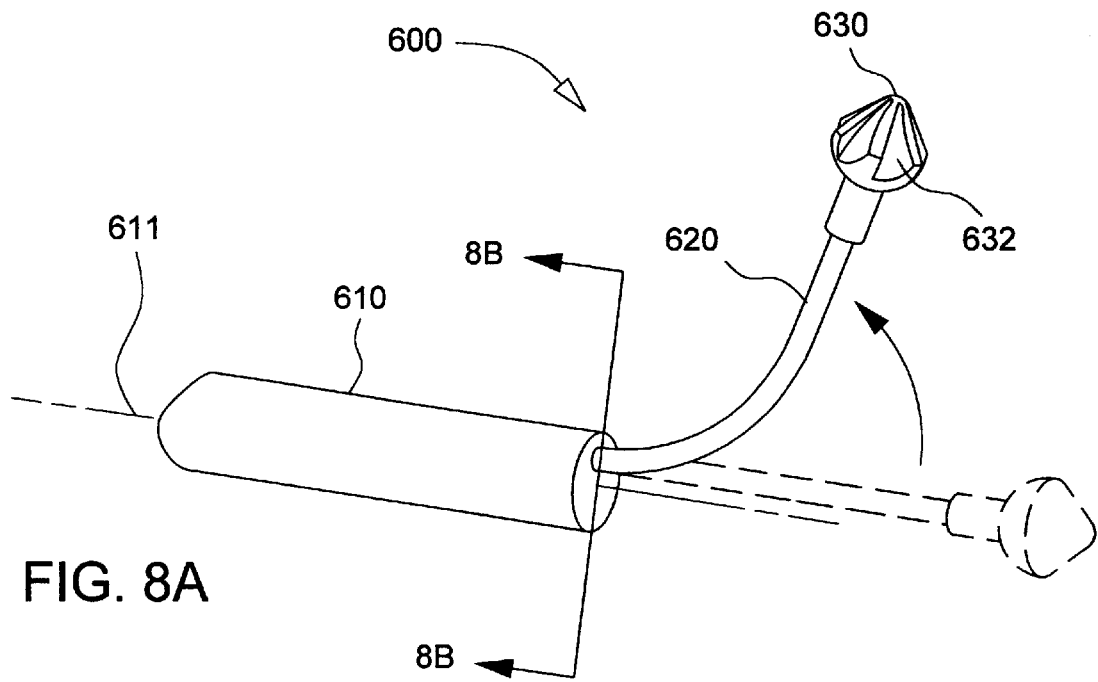
FIG. 8A is a perspective view showing a fifth embodiment of the cavitation device of the present invention.
Figure 8B:
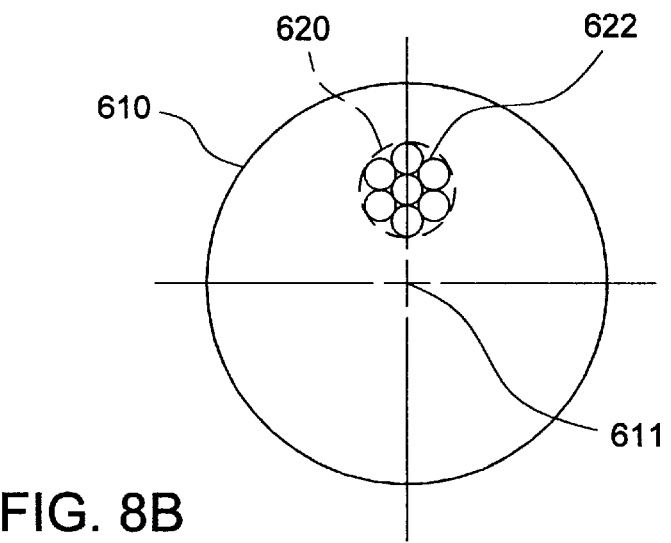
FIG. 8B is a sectional view of the device shown in FIG. 8A.

Another flexing means for biasing a flexible cutting element to move from a first shape toward a second shape is centrifugal force arising from rotational velocity of the shaft. Centrifugal force is the force that tends to impel a thing or parts of a thing outward from a center of rotation. FIG. 8A shows a fifth embodiment of the invention, cavitation device 600, comprising rotatable shaft 610 with longitudinal axis 611 and flexible cutting element 620 having a cutting tip 630 and cutting flutes 632. Flexible cutting element 620 has a generally circular cross-section. FIG. 8B shows the cross-section of flexible cutting element 620 at the distal end of shaft 610 and illustrates that flexible cutting element 620 is a standard cable structure with a uniform helical arrangement of wires 622 concentrically stranded together. This type of cable structure has high strength and high flexibility. In additional, the cable structure has a naturally abrasive quality to aid in tissue cutting. Continuing to refer to FIG. 8B, flexible cutting element 620 is shown offset from longitudinal axis 611 to further encourage outward movement of the flexible cutting element 620 under the influence of centrifugal forces that arise when shaft 610 is rotated at sufficient velocity. Surgical cable made from stainless steel or titanium alloy is readily available. It is preferred that cavitation device 600 be driven by a pneumatic surgical drill capable of rotational velocity greater than about 5,000 revolutions per minute.

Figure 9A:
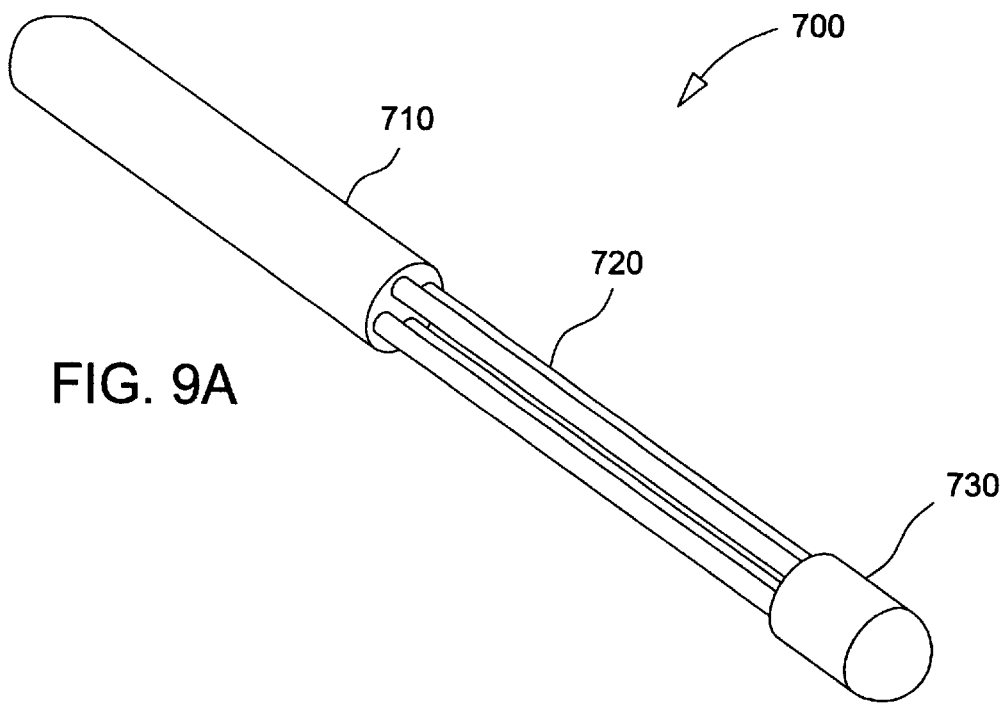
FIGS. 9A and 9B are perspective views showing a sixth embodiment of the cavitation device of the present invention.
Figure 9B:
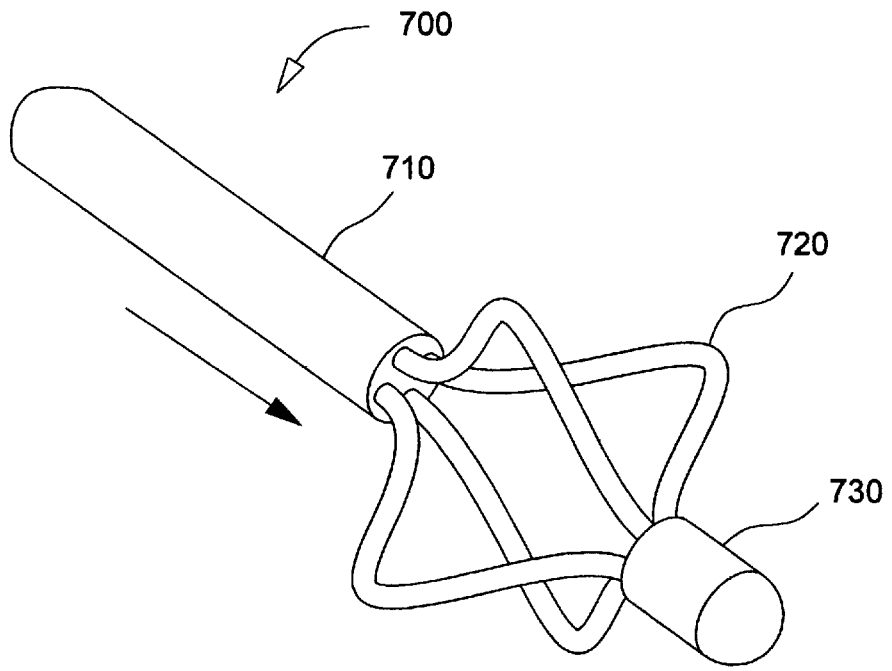

A sixth embodiment of the present invention, cavitation device 700, is shown in FIGS. 9A and 9B. Referring to FIG. 9A, a plurality of flexible cutting elements 720 are generally colinear with the rotatable shaft 710 to form a first shape suitable for minimally invasive placement of the device within tissue. The proximal ends of flexible cutting elements 720 are rigidly attached to rotatable shaft 710, and the distal ends of the flexible cutting elements 720 are attached to a spindle 730. Referring now to FIG. 9B, when cavitation device 700 is rotated at a sufficient rotational velocity, flexible cutting elements 720 have a tendency to bow outward under the influence of centrifugal force. In this embodiment, the operator can also advance rotatable shaft 710 toward spindle 730 to assist in moving the flexible cutting elements 720 from the first shape toward a second shape, in which the flexible cutting elements extend outwardly from the axis of rotation.

Additional components may be added to enhance performance in circumstances requiring a more forceful change in shape of a flexible cutting element. For example, more force is appropriate for moving fractured bone to form a tissue cavity and restore the shape of bone structures, as in the case of treating compression fractures of vertebral bodies. A cavitation device of the present invention can be adapted to provide the operator with a means to directly apply a flexing force to a flexible cutting element. FIGS. 10A and 10B show a seventh embodiment of the invention, cavitation device 800, comprise a rotatable shaft 810 having longitudinal axis 811 and flexible cutting elements 820. Rotatable shaft 810 additionally has a control passage 812 running substantially along longitudinal axis 811. A tension cable 870 is connected to flexible cutting elements 820, preferably at their distal end, and extends through the control passage 812. The proximal end of cavitation device 810 is attached to T-handle 880 having a grip 890, with the proximal end of tension cable 870 being attached to grip 890 such that rotation of grip 890 about its longitudinal axis 891 applies a tension force to tension cable 870. Thus, tension cable 870 is a flexing means for biasing flexible cutting elements 820 to move from a first shape toward a second shape. As grip 890 is rotated about its longitudinal axis 891, tension is applied to tension cable 870, thereby applying compressive and bending forces to flexible cutting elements 820 and causing them to extend outward toward a second shape. T-handle 880 also can be rotated manually about longitudinal axis 811 to form a tissue cavity.

A cavitation device of the present invention is shown in FIGS. 11A to 11F forming a cavity in osteoporotic cancellous bone followed by filling of the cavity with a strengthening synthetic bone that is injectable and hardens in situ. This method is generally applicable to all means for shape change behavior of flexible cutting elements described above. Bone structures are typically comprised of two types of bone, cortical bone and cancellous bone. Cortical bone can be considered a rigid, dense shell, whereas cancellous bone has a high degree of visible porosity. Cortical bone and cancellous bone combine to form structures that are strong and lightweight, however, osteoporosis is a disease that results in a decrease in strength due to a decrease in bone density.

Figure 11A:
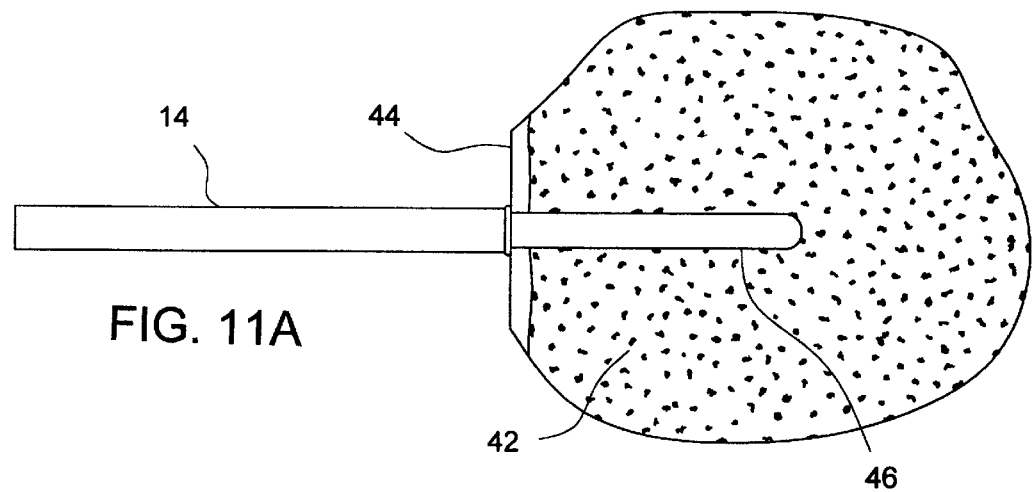
FIGS. 11A to 11F are sectional views depicting the method of using the present invention to form a cavity in bone and filling the cavity with a bone substitute material.
Figure 11B:
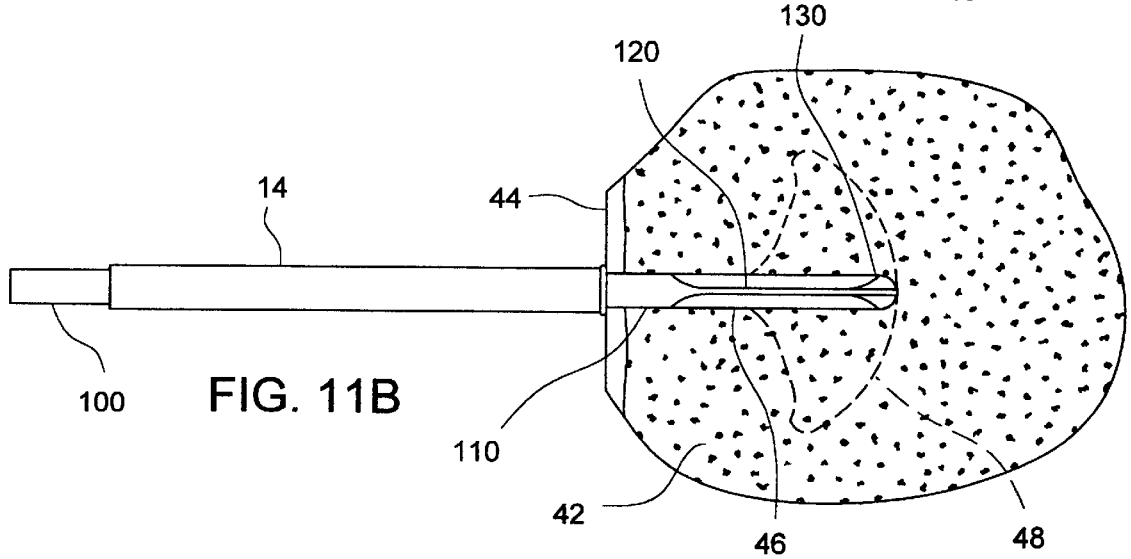
Figure 11C:
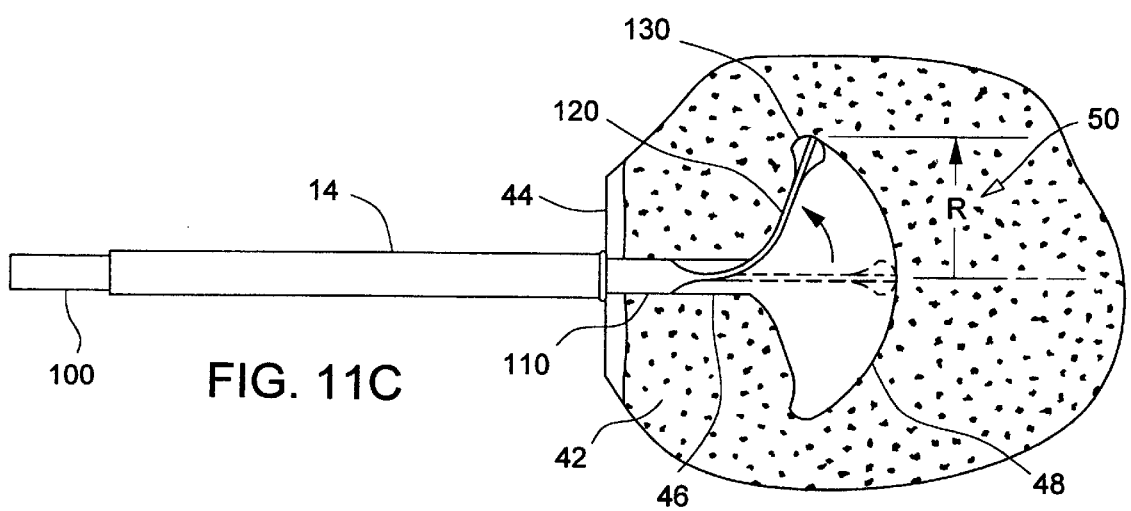
Figure 11D:
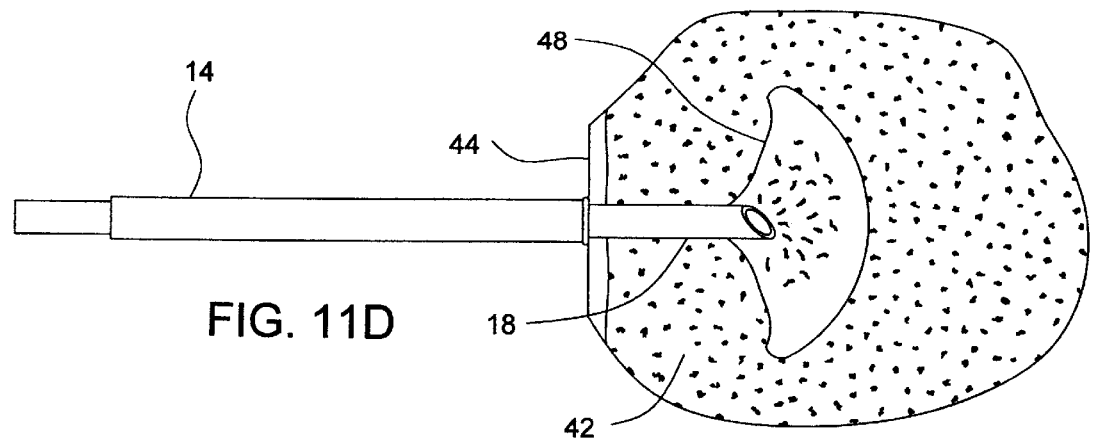
Figure 11E:
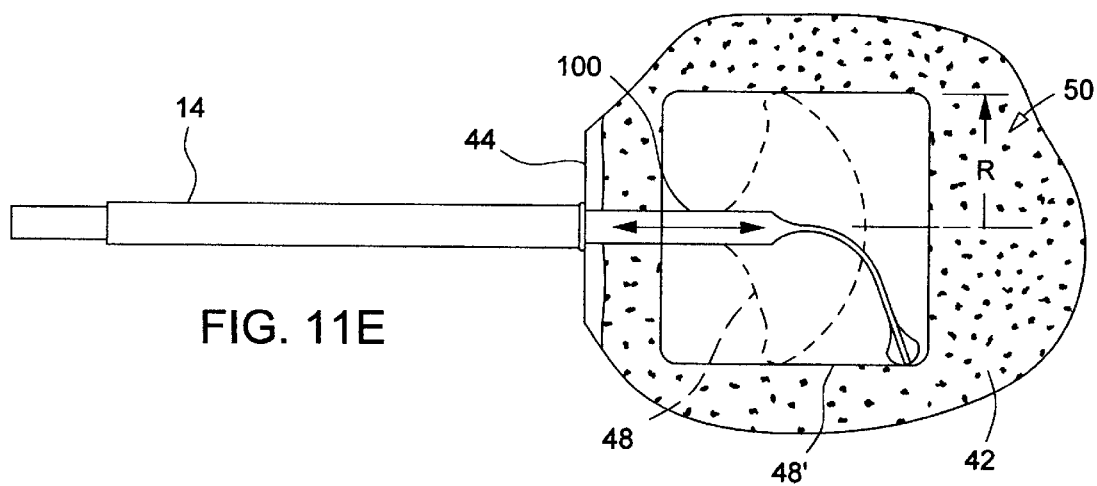
Figure 11F:
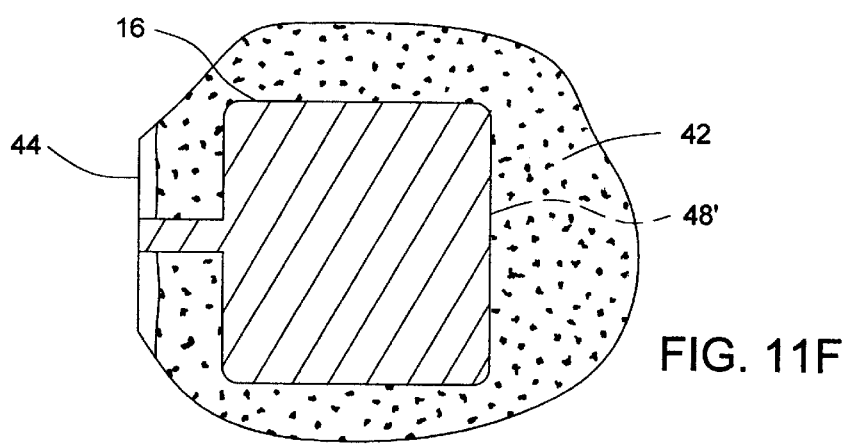

Referring specifically to FIG. 11A, through an insertion tube 14 a standard surgical drill and drill bit are used to create a pilot hole 46 in bone using established techniques. The bone structure shown in FIG. 11A includes cortical bone 44 and cancellous bone 42. A flexible cutting element 120 of cavitation device 100, shown in FIG. 11B, is in a first shape adapted for passage through insertion tube 14 to the distal end of pilot hole 46. The cutting tip 130 helps to keep flexible cutting element 120 centered during passage through insertion tube 14 and pilot hole 46. Once placed, the rotatable shaft 110 is used to transmit torsion to flexible cutting element 120. Referring now to FIG. 11C, as the rotatable shaft 110 rotates, the flexible cutting element 120 moves toward a second shape during the process of forming a generally hemispherical tissue cavity 48 with a cavity radius 50. Thus, the diameter of cavity 48 is twice the size of cavity radius 50. FIG. 11D shows the step of removing ablated tissue from the tissue cavity 48 with an irrigation tube 18 through established suction and irrigation techniques. Referring now to FIG. 11E, cavitation device 100 can be reinserted into the tissue cavity 48 and further advanced and withdrawn to create a larger tissue cavity 48'. The tissue cavity 48' of FIG. 11E is generally cylindrical, with a cavity radius 50 and a cavity diameter of twice the size of cavity radius 50. FIG. 11F shows the tissue cavity 48' filled with an injectable synthetic bone 16 that hardens in situ.

Polymethylmethacrylate (PMMA), commonly referred to as bone cement, is a well-known bone synthetic substitute that has been in use for several decades. Although PMMA has been used effectively, there continue to be concerns regarding high exothermic temperatures and potentially toxic fumes produced by PMMA during curing. Other synthetic bone substitutes have been introduced in recent years, including resorbable and non-resorbable materials. An example of a recently introduced resorbable bone substitute is injectable calcium phosphate, such as the material offered by Synthes-Stratec, Inc. under the Norian Skeletal Repair System™ brand name. An example of a non-resorbable bone substitute is injectable terpolymer resin with combeite glass-ceramic reinforcing particles, such as the material offered by Orthovita, Inc. under the Cortoss™ brand name, which is said to have strength comparable to human cortical bone.

Osteoporosis can be a contributing factor to fractures of bone, especially the femur, radius, and vertebral bodies. There are several non-invasive methods for determining bone mineral density, and patients at high risk for fracture can be identified. Patients with previous fractures related to osteoporosis are at high risk for re-fracture or initial fractures of other bone structures. Minimally invasive devices and methods, combined with synthetic bone substitutes, allow for the strengthening of bone to be practiced as a preventive treatment for patients at high risk of fracture.

The proximal end of the femur, particularly the neck region, is a common location for osteoporosis-related fractures. Referring now to FIG. 12A, a cavitation device 100 is first used to create a generally hemispherical tissue cavity 48 within the cancellous bone 42 in the head 56 of the femur 52 using the methods described above. Cavitation device 100 is removed from the tissue cavity 48 in preparation for the insertion of a second cavitation device 100'. The cutting radius associated with the second cavitation device 100' is smaller than the cutting radius of first cavitation device 100. Continuing to refer to FIG. 12A, a cavitation device 100', is shown creating a second generally cylindrical tissue cavity 48' within cancellous bone 42 in the neck 54 of a human femur 52. The resulting interconnecting tissue cavity 48/48' is filled with a strengthening synthetic bone 16, as shown in FIG. 12B. In addition, the cavitation devices and method shown in FIGS. 12A to 12B can further be adapted to the treatment of bone fractures.

There are numerous situations in orthopaedics where surgical treatment of a painful joint involves immobilization of the joint through a process called joint arthrodesis, or joint fusion. The device and method of the present invention can be used for fusion of numerous joints, including the spine or sacroiliac joint.

Figure 13A:
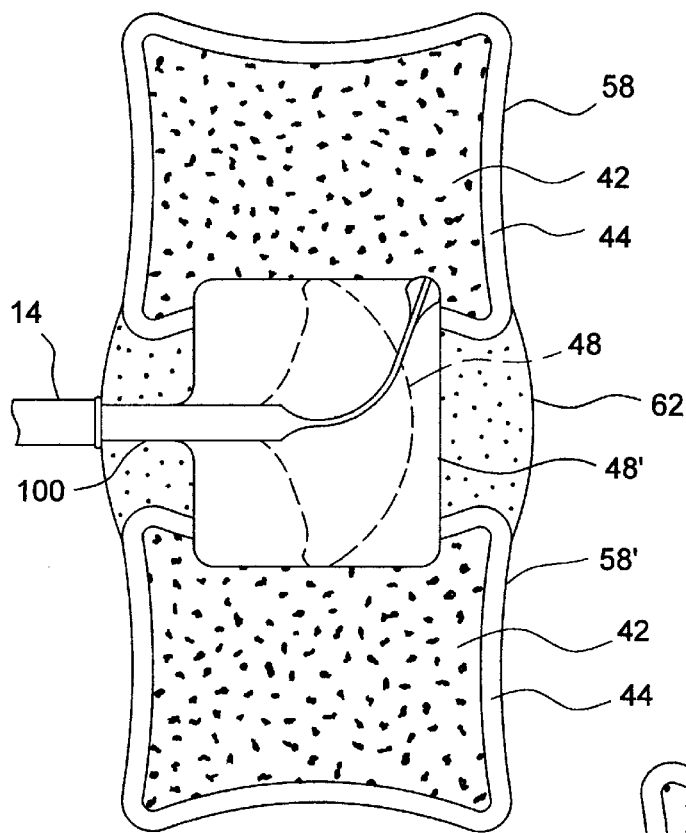
FIG. 13A is a schematic sectional view showing a cavitation device of the present invention creating a cavity between spinal vertebral bodies.
Figure 13B:
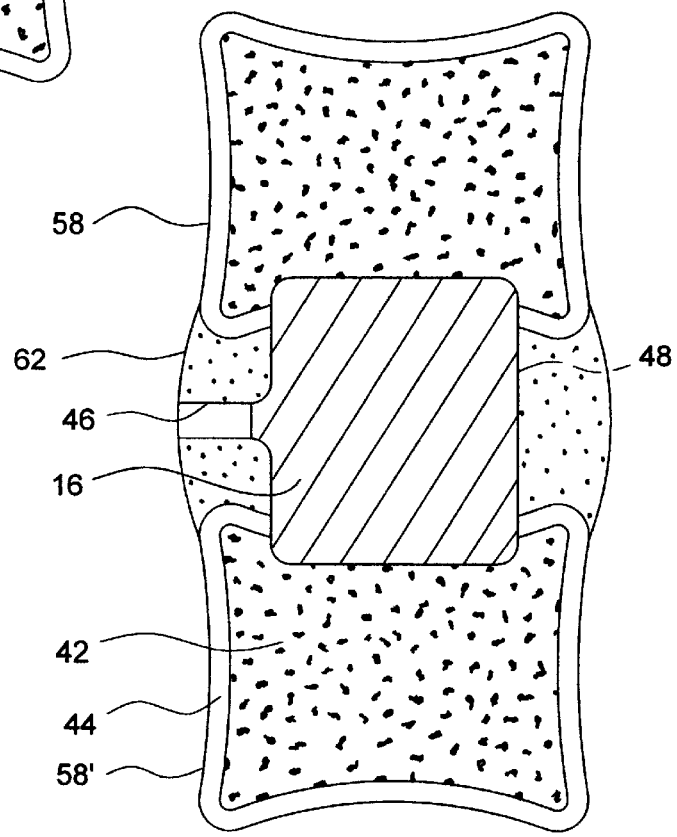
FIG. 13B shows the cavity of FIG. 13A filled with synthetic bone material to achieve joint fusion.

A spinal motion segment has numerous structures, including two vertebral bodies 58/58' and an intervertebral disc 62, as shown schematically in FIG. 13A. Using the methods previously described, cavitation device 100 is shown in FIG. 13A forming an initial generally hemispherical tissue cavity 48 that is expanded to form a generally cylindrical tissue cavity 48'. The cavitation device 100 is cutting in two types of tissue, including the bone of the vertebral bodies 58/58' and the soft tissue of the intervertebral disc 62. FIG. 13B shows the tissue cavity 48 filled with synthetic bone 16 to prevent relative motion of the vertebral bodies 58/58'. Currently, spinal fusion is typically conducted using open procedures; however, the present invention allows the process to be conducted using a less invasive percutaneous surgical procedure.

Implants, such as bone screws, anchors, pins and intramedullary nails are widely used in the orthopaedics. However, the effectiveness of such implants can be greatly diminished if their attachment to bone is not secure. Osteoporosis can lead to excessive porosity that compromises the integrity of the bone/implant interface. Loose implants are less effective and can cause additional problems if they migrate from their intended position. Local strengthening of the bone at the attachment site would be of tremendous benefit, and the present invention combined with synthetic bone substitutes addresses this problem.

Figure 14A:
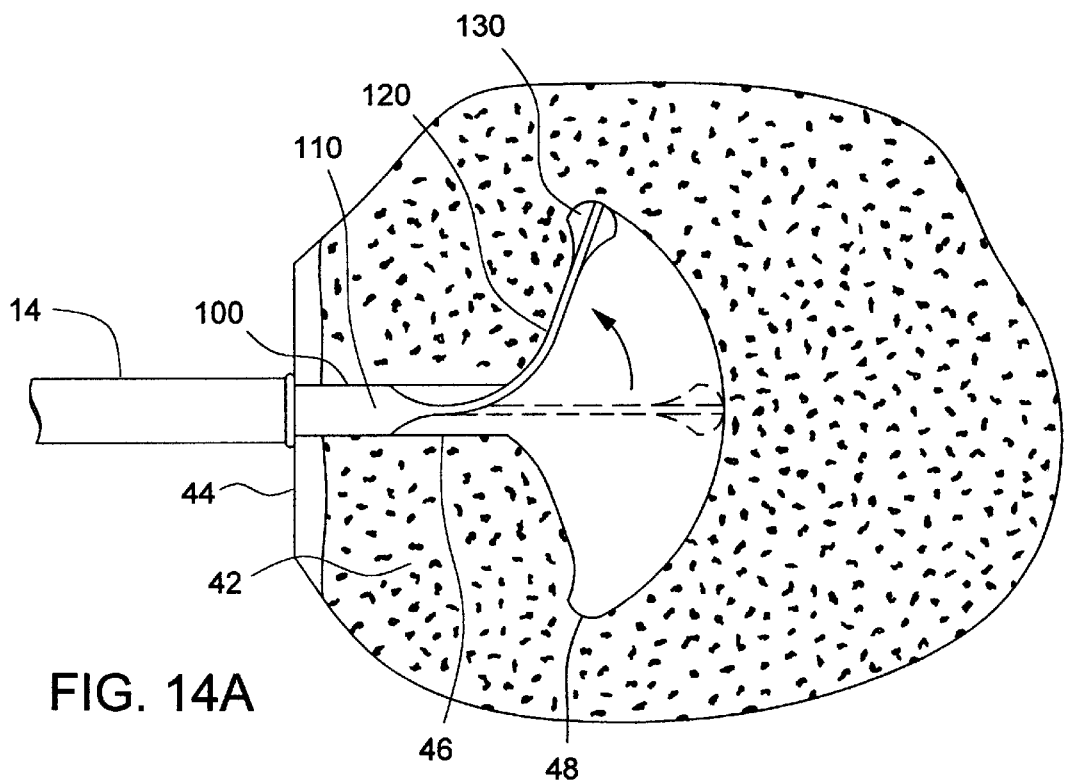
FIG. 14A is a sectional view showing a cavitation device of the present invention creating a generally hemispherical cavity within osteoporotic bone.
Figure 14B:
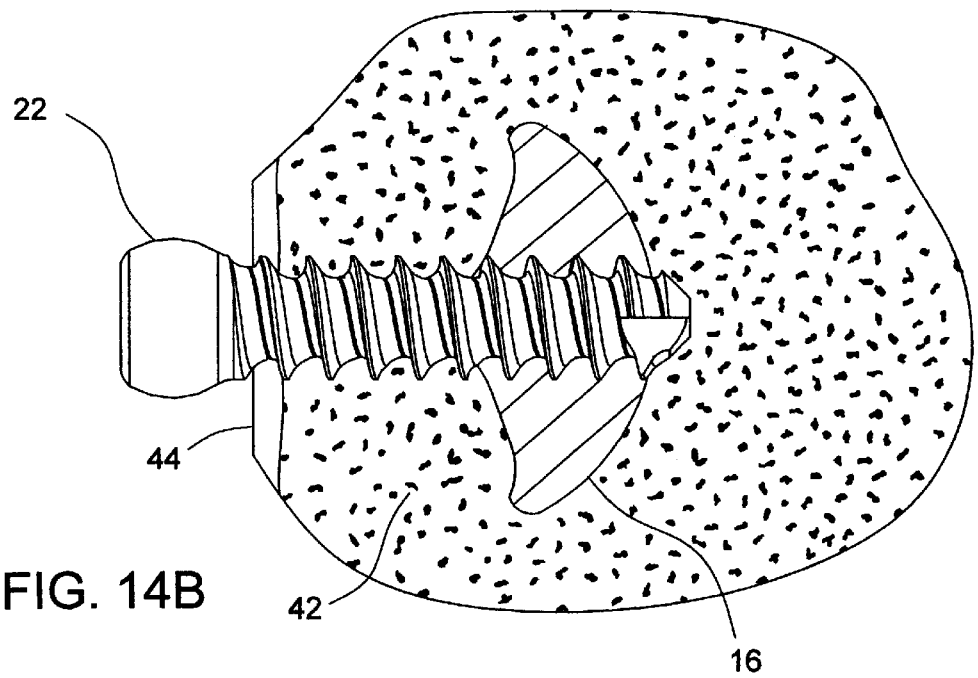
FIG. 14B shows the cavity of FIG. 14A filled with a synthetic bone substitute to strengthen the attachment of a bone screw.

Referring now to FIG. 14A, cavitation device 100 is shown creating a tissue cavity 48 in cancellous bone 42 at a site designated as an attachment location for a bone screw 22. FIG. 14B shows the tissue cavity 48 filled with synthetic bone 16, and the bone screw 22 has been placed substantially within the synthetic bone 16. An important aspect of the present invention and method is the preservation of cortical bone 44. The preceding methods and devices can be part of a planned surgical procedure, or as part of a salvage procedure when the surgeon experiences unanticipated stripping of bone during tightening of a bone screw.

Figure 15:
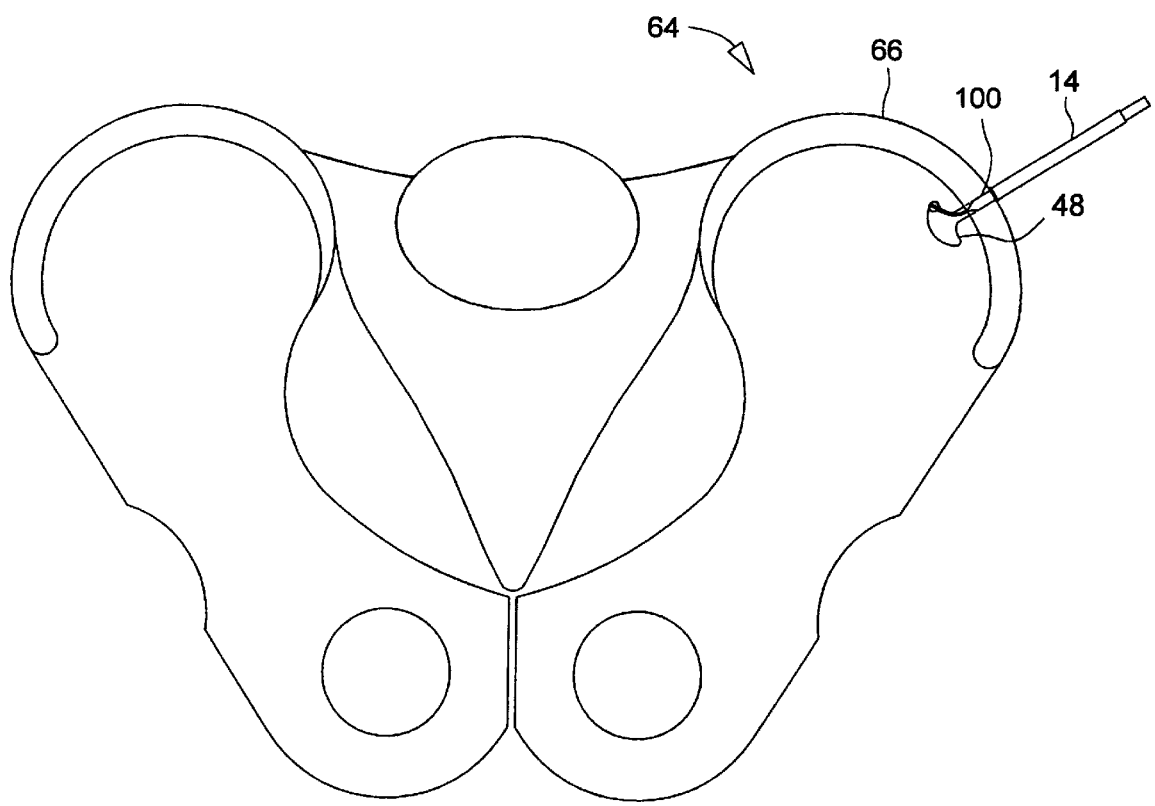
FIG. 15 shows a schematic representation of the human pelvis and the cavitation device of the present invention harvesting bone from the iliac crest by minimally invasive surgical techniques.

To repair or fuse bone, surgeons often harvest bone from a second surgical site. Compared to allograft and current bone substitutes, autogenous bone graft provides all the cells, proteins, and matrix required to form new bone. Because of the morbidity associated with open procedures for harvesting bone, the trend is toward minimally invasive techniques associated with percutaneous instrumentation. The present invention allows for minimally invasive access to bone for harvesting. The dynamic shape behavior of the present invention will allow the technology to move toward less invasive instruments with smaller working diameters. Referring now to the FIG. 15, the most common site for bone harvest is the iliac crest 66 of the pelvis 64. A cavitation device 100 is shown in the region of the iliac crest 66 creating a tissue cavity 48. Emulsified bone may be removed from the tissue cavity 48 using known irrigation and suction techniques. The harvested bone will have a consistency similar to putty, a desirable form for numerous orthopaedic applications to include the filling of a bone deficit or joint fusion.

From the description above, a number of advantages of our invention become evident. The flexible cutting element of the invention eliminates the need for complex assemblies with numerous moving parts. Additionally, the shape-changing behavior of the flexible cutting element enables percutaneous passage through an insertion tube. The shape change behavior also improves cutting efficiency by providing a forceful press of a flexible cutting element against the tissue during formation of a cavity. The cavitation device of the present invention can be further adapted in multi-component configurations to provide the operator with a means for forcefully actuating a flexible cutting element on demand. The device and methods of the present invention are minimally invasive and have many applications, especially in orthopaedics.

The preferred embodiments presented in this disclosure are examples. Those skilled in the art can develop modifications and variants that do not depart from the spirit and scope of the disclosed cavitation devices and methods. For example, there are instances where an insertion tube is not required and a pilot hole in bone tissue is appropriate for passage to the cavitation site. Disclosed flexing means for biasing the flexible cutting elements to move from a first shape to a second shape include elastic deformation, thermal shape-memory, centrifugal force, and force applied through a tension cable. Although these means are considered in the examples separately, cavitation devices of the present invention can comprise a combination of two or more of these means. Those skilled in the art will understand that markings on the shaft of a cavitation device of the invention can be used for indicating depth of insertion and that an additional fitting on the shaft can be used to limit the depth of insertion. Additional variants, also with the spirit and scope of the invention, include flexible cutting elements slidably connected to the shaft, such that the length of a flexible cutting element can be adjusted. Thus the scope of the invention should be determined by the appended claims and their legal equivalents, rather than by the examples given.

We claim:

1. A tissue cavitation device, comprising:

a shaft having a diameter and a longitudinal axis;

a flexible cutting element associated with said shaft;

said flexible cutting element adapted to assume a first shape substantially colinear with the longitudinal axis of said shaft and adapted to assume a second shape suitable for forming a tissue cavity having a diameter greater than the diameter of said shaft when said shaft is rotated about the longitudinal axis of said shaft; and spring bias arising from elastic deformation of said flexible cutting element when waid flexible cutting element is in said first shape, biasing said flexible cutting element to move from said first shape toward said second shape.

2. The device of claim 1, wherein said flexible cutting element has a substantially quadrilateral cross-section.

3. The device of claim 1, wherein said flexible cutting element has a substantially circular cross-section.

4. The device of claim 1, wherein said shaft and said flexible cutting element are dimensioned to pass telescopically through the interior of an insertion tube having a proximal end and a distal end.

5. The device of claim 4, wherein said flexible cutting element assumes said first shape when said flexible cutting element is positioned within said insertion tube, and said spring bias tends to move said flexible cutting element toward said second shape as said flexible cutting element emerges from the distal end of said insertion tube.

6. The device of claim 1, wherein said shaft has a first end and a second end;

said flexible cutting element is disposed at the second end of said shaft; and at least a portion of said flexible cutting element moves away from the longitudinal axis of said shaft as said flexible cutting element moves from said first shape toward said second shape.

7. The device of claim 6, wherein said flexible cutting element is rigidly connected to the second end of said shaft.

8. The device of claim 7, wherein said flexible cutting element and said shaft are formed from a single piece of material.

9. The device of claim 8, wherein said second shape of said flexible cutting element comprises a curvilinear arc projecting away from the longitudinal axis of said shaft.

10. The device of claim 9, wherein said shaft has a substantially circular cross-section.

11. The device of claim 9, wherein said shaft has a substantially square cross-section.

12. The device of claim 1, wherein said flexible cutting element has at least one cutting flute.

13. The device of claim 12, wherein said flexible cutting element has a free end, and the at least one cutting flute of said flexible cutting element is disposed at the free end of said flexible cutting element.

14. The device of claim 1, wherein said flexible cutting element has at least one serration.

15. A tissue cavitation device comprising:

a shaft having a diameter and a longitudinal axis;

a flexible cutting element, formed from a shape memory alloy, associated with said shaft;

said flexible cutting element adapted to assume a first shape substantially colinear with the longitudinal axis of said shaft and adapted to assume a second shape suitable for forming a tissue cavity having a diameter greater than the diameter of said shaft when said shaft is rotated about the longitudinal axis of said shaft; and shape memory behavior of said shape memory alloy in response to the transfer of heat to said flexible cutting element biasing said flexible cutting element to move from said first shape toward waid second shape.

16. The device of claim 15, wherein said flexible cutting element has a substantially quadrilateral cross-section.

17. The device of claim 15, wherein said flexible cutting element has a substantially circular cross-section.

18. The device of claim 15, wherein said heat is body heat transferred to said flexible cutting element as said flexible cutting element is inserted into tissue.

19. The device of claim 15, wherein said heat is frictional heat generated as said flexible cutting element cuts tissue upon rotation of said shaft.

20. The device of claim 15, wherein said shaft and said flexible cutting element are dimensioned to pass telescopically through the interior of an insertion tube having a proximal end and a distal end.

21. The device of claim 15, wherein said shaft has a first end and a second end;

said flexible cutting element is disposed at the second end of said shaft; and at least a portion of said flexible cutting element moves away from the longitudinal axis of said shaft as said flexible cutting element moves from said first shape toward said second shape.

22. The device of claim 21, wherein said flexible cutting element is rigidly connected to the second end of said shaft.

23. The device of claim 22, wherein said flexible cutting element and said shaft are formed from a single piece of material.

24. The device of claim 23, wherein said second shape of said flexible cutting element comprises a curvilinear arc projecting away from the longitudinal axis of said shaft.

25. The device of claim 24, wherein said shaft has a substantially circular cross-section.

26. The device of claim 24, wherein said shaft has a substantially square cross-section.

27. The device of claim 18, wherein said flexible cutting element has at least one cutting flute.

28. The device of claim 27, wherein said flexible cutting element has a free end, and the at least one cutting flute of said flexible cutting element is disposed at the free end of said flexible cutting element.

29. The device of claim 15, wherein said flexible cutting element has at least one serration.

30. The device of claim 15, wherein said shape memory alloy is Nitinol.

31. A tissue cavitation device, comprising:

a shaft having a diameter and a longitudinal axis;

a flexible cutting element associated with said shaft having a free end and a cutting tip disposed on the free end of the cutting element;

said flexible cutting element adapted to assume a first shape substantially colinear with the longitudinal axis of said shaft and adapted to assume a second shape comprising a curvilinear arc projecting away from the longitudinal axis of said shaft, whereby spring bias arising from elastic deformation when said flexible cutting element is in said first shape tends to move said flexible cutting element from said first shape toward said second shape, thereby enabling said flexible cutting element to form a tissue cavity having a diameter greater than the diameter of said shaft when said shaft is rotated about the longitudinal axis of said shaft.

32. The device of claim 31, wherein said flexible cutting element has a substantially quadrilateral cross-section.

33. The device of claim 31, wherein said flexible cutting element has a substantially circular cross-section.

34. The device of claim 31, wherein said shaft and said flexible cutting element are dimensioned to pass telescopically through the interior of an insertion tube having a proximal end and a distal end.

35. The device of claim 34, wherein said flexible cutting element assumes said first shape when said flexible cutting element is positioned within said insertion tube, and said spring bias tends to move said flexible cutting element from said first shape toward said second shape as said cutting element emerges from the distal end of said insertion tube.

36. The device of claim 31, wherein said flexible cutting element is rigidly connected to said shaft.

37. The device of claim 36, wherein said flexible cutting element and said shaft are formed from a single piece of material.

38. The device of claim 31, wherein said flexible cutting element has at least one cutting flute.

39. The device of claim 38, wherein said flexible cutting element has a free end, and said at least one cutting flute is disposed at the free end of said flexible cutting element.

40. The device of claim 31, wherein said flexible cutting element has at least one serration.

41. The device of claim 31, wherein said shaft has a substantially circular cross-section.

42. The device of claim 31, wherein said shaft has a substantially square cross-section.

43. A tissue cavitation device, comprising:

a shaft having a diameter and a longitudinal axis;

a flexible cutting element associated with said shaft and formed from a shape memory alloy;

said flexible cutting element adapted to assume a first shape substantially colinear with the longitudinal axis of said shaft and adapted to assume a second shape comprising a curvilinear arc projecting away from the longitudinal axis of said shaft, whereby shape memory behavior of said shape memory alloy biases said flexible cutting element to move from said first shape toward said second shape, thereby enabling said flexible cutting element to form a tissue cavity having a diameter greater than the diameter of said shaft when said shaft is rotated about the longitudinal axis of said shaft.

44. The device of claim 43, wherein said flexible cutting element has a substantially quadrilateral cross-section.

45. The device of claim 43, wherein said flexible cutting element has a substantially circular cross-section.

46. The device of claim 43, wherein said shape memory behavior is activated by the transfer of heat to said flexible cutting element.

47. The device of claim 45, wherein said heat is body heat transferred to said flexible cutting element as said flexible cutting element is inserted into tissue.

48. The device of claim 45, wherein said heat is frictional heat generated as said flexible cutting element cuts tissue upon rotation of said shaft.

49. The device of claim 43, wherein said shape memory alloy is Nitinol.

50. The device of claim 43, wherein said flexible cutting element is rigidly connected to said shaft.

51. The device of claim 50, wherein said flexible cutting element and said shaft are formed from a single piece of material.

52. The device of claim 43, wherein said flexible cutting element has at least one cutting flute.

53. The device of claim 52, wherein said flexible cutting element has a free end, and said at least one cutting flute is disposed at the free end of said flexible cutting element.

54. The device of claim 43, wherein said flexible cutting element has at least one serration.

55. The device of claim 43, wherein said shaft has a substantially circular cross-section.

56. The device of claim 43, wherein said shaft has a substantially square cross-section.

57. A tissue cavitation device, comprising:

a shaft having a diameter and a longitudinal axis;

a flexible cutting element rigidly connected to said shaft;

said flexible cutting element adapted to assume a first shape substantially colinear with the longitudinal axis of said shaft and adapted to assume a second shape comprising a curvilinear arc projecting away from the longitudinal axis of said shaft, whereby centrifugal force arising from rotation of said shaft about the longitudinal axis of said shaft tends to move said flexible cutting element from said first shape toward said second shape, thereby enabling said flexible cutting element to form a tissue cavity having a diameter greater than the diameter of said shaft when said shaft is rotated about the longitudinal axis of said shaft.

58. The device of claim 57, wherein said flexible cutting element is offset from the longitudinal axis of said shaft.

59. The device of claim 57, wherein said shaft and said flexible cutting element are dimensioned to pass telescopically through the interior of an insertion tube having a proximal end and a distal end.

60. The device of claim 57, wherein said flexible cutting element is a cable.

61. The device of claim 57, wherein said flexible cutting element has at least one cutting flute.

62. The device of claim 61, wherein said flexible cutting element has a free end, and said at least one cutting flute is disposed at the free end of said flexible cutting element.

63. The device of claim 57, wherein said shaft has a substantially circular cross-section.

64. The device of claim 57, wherein said shaft has a substantially square cross-section.

\* \* \* \* \*